United States Patent [19]
Lawson et al.

[11] Patent Number: 5,260,286
[45] Date of Patent: Nov. 9, 1993

[54] 2-PIPERIDINECARBOXYLIC ACID DERIVATIVES USEFUL AS NMDA RECEPTOR ANTAGONISTS

[75] Inventors: John A. Lawson, Redwood City; Anjali Pandey, Menlo Park; Dennis Yasuda, Campbell; Masato Tanabe, Palo Alto, all of Calif.

[73] Assignee: Japan Tobacco, Inc., Tokyo, Japan

[21] Appl. No.: 961,811

[22] Filed: Oct. 16, 1992

[51] Int. Cl.$^5$ .................. C07F 9/06; C07F 9/38; A61K 31/675
[52] U.S. Cl. ........................................ 514/89; 546/22
[58] Field of Search ........................... 514/89; 546/22

[56] References Cited

U.S. PATENT DOCUMENTS

| | | | |
|---|---|---|---|
| 4,108,857 | 8/1978 | Albertson | 260/293.54 |
| 4,746,653 | 5/1988 | Hutchinson et al. | 514/89 |
| 4,837,226 | 6/1989 | Coughenour et al. | 514/443 |
| 4,898,854 | 2/1990 | Hutchinson et al. | 514/89 |
| 4,906,621 | 3/1990 | Hutchinson et al. | 514/89 |
| 4,916,125 | 4/1990 | Herrling et al. | 514/89 |

FOREIGN PATENT DOCUMENTS

| | | | |
|---|---|---|---|
| 0159889 | 10/1985 | European Pat. Off. | |
| 0203891 | 12/1986 | European Pat. Off. | |
| 0275820 | 7/1988 | European Pat. Off. | 546/22 |
| 3804936 | 11/1988 | Fed. Rep. of Germany | |
| WO89/09209 | 10/1989 | PCT Int'l Appl. | |
| 1043859 | 3/1965 | United Kingdom | |
| 1233193 | 8/1968 | United Kingdom | |
| 1233194 | 8/1968 | United Kingdom | |

*Primary Examiner*—C. Warren Ivy
*Assistant Examiner*—A. A. Owens
*Attorney, Agent, or Firm*—Morrison & Foerster

[57] ABSTRACT

Compounds of formula I

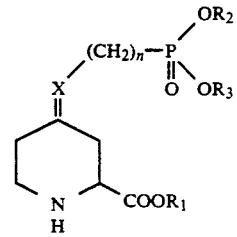

wherein X is

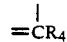

or =N—O—, in which $R_4$ is hydrogen or halogen, $R_1$, $R_2$, and $R_3$ independently represent hydrogen or a $C_{1-4}$ alkyl group, and n has a value of zero to four are disclosed. Also disclosed are pharmaceutically acceptable salts of these compounds, pharmaceutical compositions of these compounds or salts with a pharmaceutically acceptable carrier, the use of these materials as N-methyl-D-aspartate receptor antagonists, processes for preparing these compounds and salts, and methods to treat cerebral diseases by administering an effective amount of these compounds, salts or compositions.

9 Claims, 3 Drawing Sheets

Scheme 1

Scheme 2

2-PIPERIDINECARBOXYLIC ACID DERIVATIVES USEFUL AS NMDA RECEPTOR ANTAGONISTS

BACKGROUND OF THE INVENTION

1. Field of the Invention

The invention concerns a series of 4-(phosphonoalkylidene)- or 4-(phosphonoalkoxyimino)-2-piperidinecarboxylic acid derivatives useful in the treatment of cerebrovascular disorders.

2. Background Information

Excessive excitation by neurotransmitters can cause the degeneration and death of neurons. It is believed that this excitotoxic action is mediated by the excitatory amino acids, glutamate and aspartate, acting at the N-methyl-D-aspartate (NMDA) receptor. This excitotoxic action is responsible for neuronal loss in cerebrovascular disorders such as cerebral ischemia or cerebral infarction resulting from a range of conditions such as thromboembolic or hemorrhagic stroke, cerebral vasospasm, hypoglycemia, cardiac arrest, status epilepticus, perinatal asphyxia, anoxia such as from drowning, pulmonary surgery and cerebral trauma.

The compounds of the invention, which are active as competitive antagonists of NMDA receptor-mediated ion-channel activation, are thus useful in the treatment of the above disorders. In addition, by this NMDA receptor antagonist action, the compounds of the invention are also useful for treating neurodegenerative disorders, spinal cord injury, and poisoning by exogenous NMDA poisons (for example, some forms of lathyrism). There are no specific therapies for these neurodegenerative disorders, but competitive and noncompetitive NMDA antagonists acting specifically to antagonize excitatory neurotransmission at NMDA receptors offer a novel therapeutic approach to these disorders; B. Meldrum in *Neurotoxins and Their Pharmacological Implications.* ed. P. Jenner, Raven Press, New York, 1987.

Recent reports in the literature have confirmed the protective action of certain NMDA antagonists in pharmacological models of neurodegenerative disorders (J. W. McDonald, F. S. Silverstein, and M. V. Johnston, *Eur. J. Pharmacol.,* (1987) 140:359; R. Gill, A. C. Foster and G. N. Woodruff, *J. Neurosci.,* (1987) 7:3343; S. M. Rothman, J. Thurston, R. E. Hauhart, G. D. Clark and J. S. Solomon, *Neurosci.,* (1987) 21:673; M. P. Goldberg, P. C. Pham and D. W. Choi, *Neurosci. Lett.,* (1987) 80:11).

In addition, U.S. Pat. Nos. 4,746,653; 4,906,621; and 4,898,854 are concerned with phosphonic acid derivatives of 2-piperidine or 2-tetrahydropyridine carboxylates, which are said to be useful as N-methyl-D-aspartate (NMDA) receptor antagonists.

STATEMENT OF THE INVENTION

The invention relates to compounds of the following General Formula I:

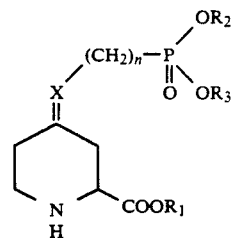

wherein X is

or $=N-O-$, in which $R_4$ is hydrogen or halogen, $R_1$, $R_2$, and $R_3$ independently represent hydrogen or a $C_{1-4}$ alkyl group, and n is an integer having a value of zero to four and to pharmaceutically acceptable salts of the compounds of Formula I, and pharmaceutical compositions made up of these compounds and salts with pharmaceutically acceptable carriers. These compositions are useful as N-methyl-D-aspartate receptor antagonists. In other aspects, this invention provides processes for preparing these compounds and salts, and methods to treat cerebral diseases by administering to a patient an effective amount of these pharmaceutical compositions.

DETAILED DESCRIPTION OF THE INVENTION

BRIEF DESCRIPTION OF THE DRAWINGS

This invention will be described with reference to the accompanying drawings in which.

DESCRIPTION OF PREFERRED EMBODIMENTS

Figure 1:
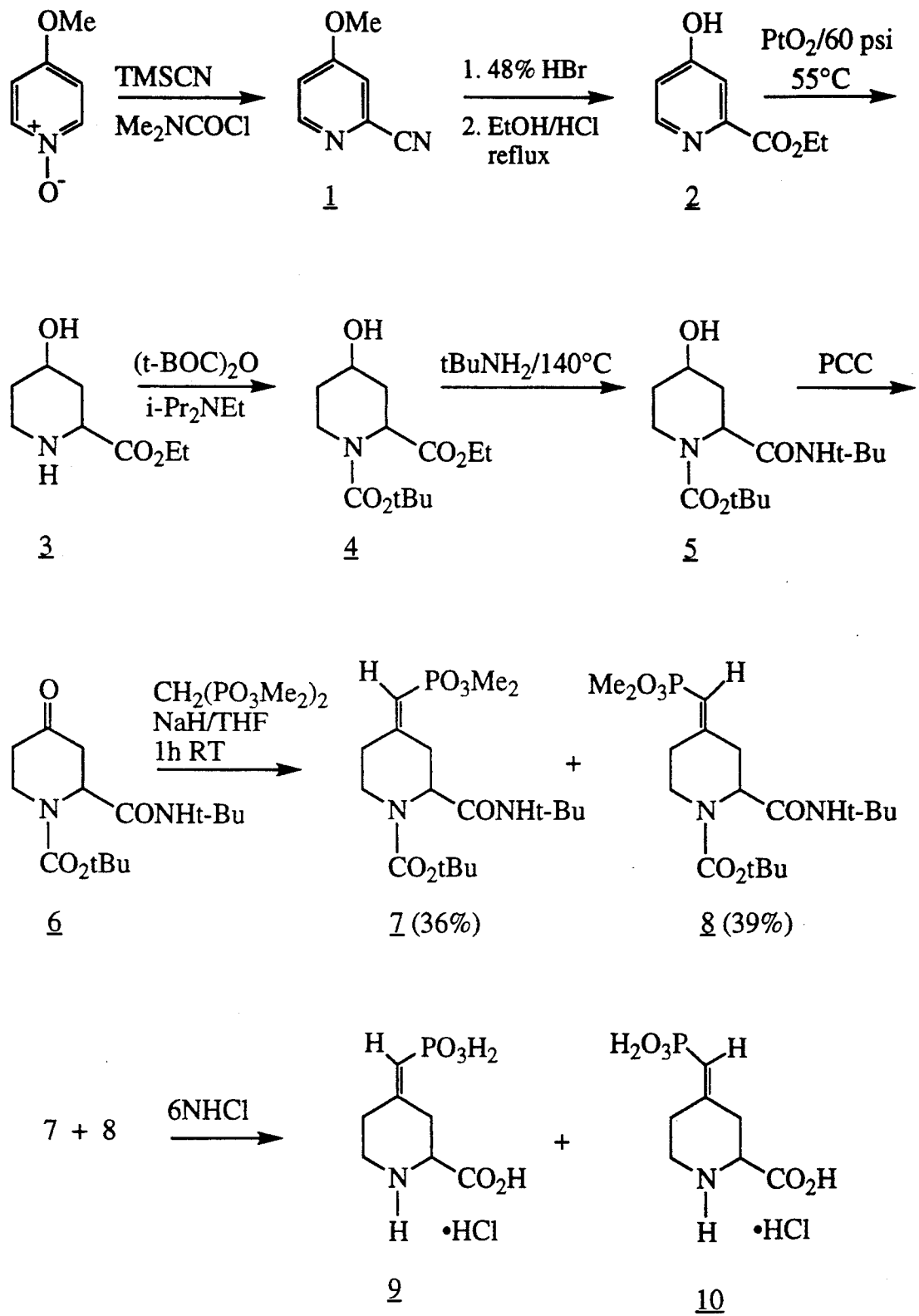
FIG. 1 is a reaction scheme for preparing compounds and salts of the invention as set out in Example 1.

The present invention provides compounds and pharmaceutical compositions based on them which are useful as N-methyl-D-aspartate receptor antagonists and in the treatment of cerebral diseases such as cerebral ischemia, cerebral hypoglycemia, epilepsy, anxiety and convulsion.

The Compounds

The compounds of this invention are materials of General Formula I, and pharmaceutically acceptable salts thereof:

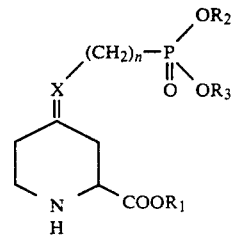

In this formula X is

or =N—O— wherein $R_4$ is hydrogen or a halo, such as fluoro, chloro, bromo or the like. When $R_4$ is present, it is preferably hydrogen or fluoro. "n" is an integer. It can be 0, 1, 2, 3, or 4. $R_1$ is hydrogen or a $C_{1-4}$ alkyl. The term "$C_{1-4}$ alkyl" means a saturated aliphatic group Of 1, 2, 3 or 4 carbons, either branched or straight chain. "$C_{1-4}$ alkyls" include methyl, ethyl, n-propyl, i-propyl, n-butyl, i-butyl, sec-butyl and tert-butyl groups.

$R_2$ and $R_3$ are also hydrogen or $C_{1-4}$ alkyls $R_1$, $R_2$ and $R_3$ are selected independently, but usually, for ease of synthesis, $R_2$ and $R_3$ are the same. Methyl and hydrogen are preferred as $R_2$ and $R_3$ groups.

Pharmaceutically Acceptable Salts

These compounds can exist as salts. The salt can be formed of the carboxylic acid (i.e., a salt anion replacing a hydrogen $R_1$), and salts can be formed of the phosphonic acid (i.e., replacing the $R_2$ and/or the $R_3$ groups if they are hydrogens with a salt anion). All three positions can be salts.

Pharmaceutically acceptable salts are salts of these compounds which have anions that are pharmaceutically acceptable—i.e., nontoxic. These are preferably metal or ammonium salts of the compounds of the invention having a free phosphono or/and carboxyl group, more particularly alkali metal or alkaline earth metal salts such as the sodium, potassium, magnesium or calcium salt; or advantageously crystallizing ammonium salts derived from ammonia or organic amines, such as monoethylamine, diethylamine, triethylamine, dicyclohexylamine, triethanolamine, ethylenediamine, tris-(hydroxymethyl)aminoethane or benzyltrimethylammonium hydroxide. In addition, the NH group present in the compounds of the invention can form acid-addition salts of pharmaceutically acceptable inorganic or organic acids, such as of strong mineral acids, for example, hydrohalic, hydrochloric or hydrobromic acid; sulfuric, phosphoric or nitric acid; aliphatic or aromatic carboxylic or sulfonic acid, for example, acetic, propionic, succinic, glycolic, lactic, malic, tartaric, gluconic, citric, ascorbic, maleic, fumaric, pyruvic, palmoic, nicotinic, methanesulfonic, ethanesulfonic, hydroxyethanesulfonic, benzenesulfonic, p-toluenesulfonic or naphthalenesulfonic acid.

Isomers, etc.

The compounds of the invention contain at least one asymmetric carbon atom. The invention includes individual enantiomers, diastereomers, or mixtures thereof, which may be prepared or isolated by methods known in the art. The compounds of the invention also include geometrical isomers based on the olefin or imine portion. The invention includes individual E-isomers, Z-isomers and mixtures thereof, which may be prepared or isolated by the methods known in the art.

Pharmaceutical Formulations

The compounds of the invention may be administered according to any convenient or effective methods for introducing foreign substances into the blood stream of mammals, such as by oral, rectal, nasal, buccal, vaginal, or parenteral routes. The effective dosage level is, for example, 0.01 to 100 mg/kg, preferably about 0.05 to 50 mg/kg, and may be administered on a regimen of 1-4 times per day. The pharmaceutical formulations comprising the compounds of the invention may be in dosage forms such as tablets, pills, capsules, powders, or granules for oral administration.

Compounds and salts here provided can be formulated into pharmaceutical compositions by admixture with pharmaceutically acceptable nontoxic carriers. As mentioned above, such compositions may be prepared for use for parenteral (subcutaneous, intramuscular or intravenous) administration particularly in the form of liquid solutions or suspensions; for use in vaginal or rectal administration particularly in semisolid forms such as creams and suppositories; for oral or buccal administration particularly in the form of tablets or capsules; or intranasally particularly in the form of powders, nasal drops or aerosols.

The compositions may conveniently be administered in unit dosage form and may be prepared by any of the methods well known in the pharmaceutical art, for example as described in *Remingtons's Pharmaceutical Sciences*, Mack Publishing Company, Easton, Pa. 1975, incorporated by reference. Formulations for parenteral administration may contain as common excipients, sterile water or saline, polyalkylene glycols such as polyethylene glycol, oils of vegetable origin, hydrogenated naphthalenes and the like. Formulations for vaginal or rectal administration, e.g., suppositories, may contain as excipients, for example, polyalkylene glycols, petroleum jelly, cocoa butter, and the like. Formulations for inhalation administration may be solid and contain as excipients, for example, lactose, or may be aqueous or oily solutions for administration in the form of nasal drops. For buccal administration typical excipients include sugars, calcium stearate, magnesium stearate, pregelatinated starch, and the like.

For oral administration, a pharmaceutically acceptable nontoxic composition can be formed by the incorporation of any of the normally employed excipients, oral dose extenders or carriers such as, for example, pharmaceutical grades of mannitol, lactose, starch, magnesium stearate, sodium saccharin, talcum, cellulose, glucose, sucrose, magnesium, carbonate, and the like. Such compositions can take the form of solutions, suspensions, tablets, pills, capsules, powders, sustained-release formulations, and the like. Such compositions may contain 0.1-95% active ingredient, preferably 1-70%, with the remainder being carrier.

The materials of this invention can be employed as the sole active agent in a pharmaceutical composition or can be used in combination with other active ingredients.

The effects of the compounds of the invention can be evaluated in in vitro tests or in vivo animal tests using mammals such as mice, rats, rabbits, dogs and monkeys, or tissues, membranes, receptors or enzyme preparations thereof.

Competition binding for NMDA receptor with radiolabeled known NMDA antagonist is one convenient way to ascertain the ability of the compounds of the invention to bind to target cerebral cells. This evaluation can be made according to the method of J. Lehman et al., 1988. In addition, the ability to antagonize NMDA receptors can be evaluated according to the method of Ferkany et al., 1988.

Preparation of the Compounds

Figure 2:
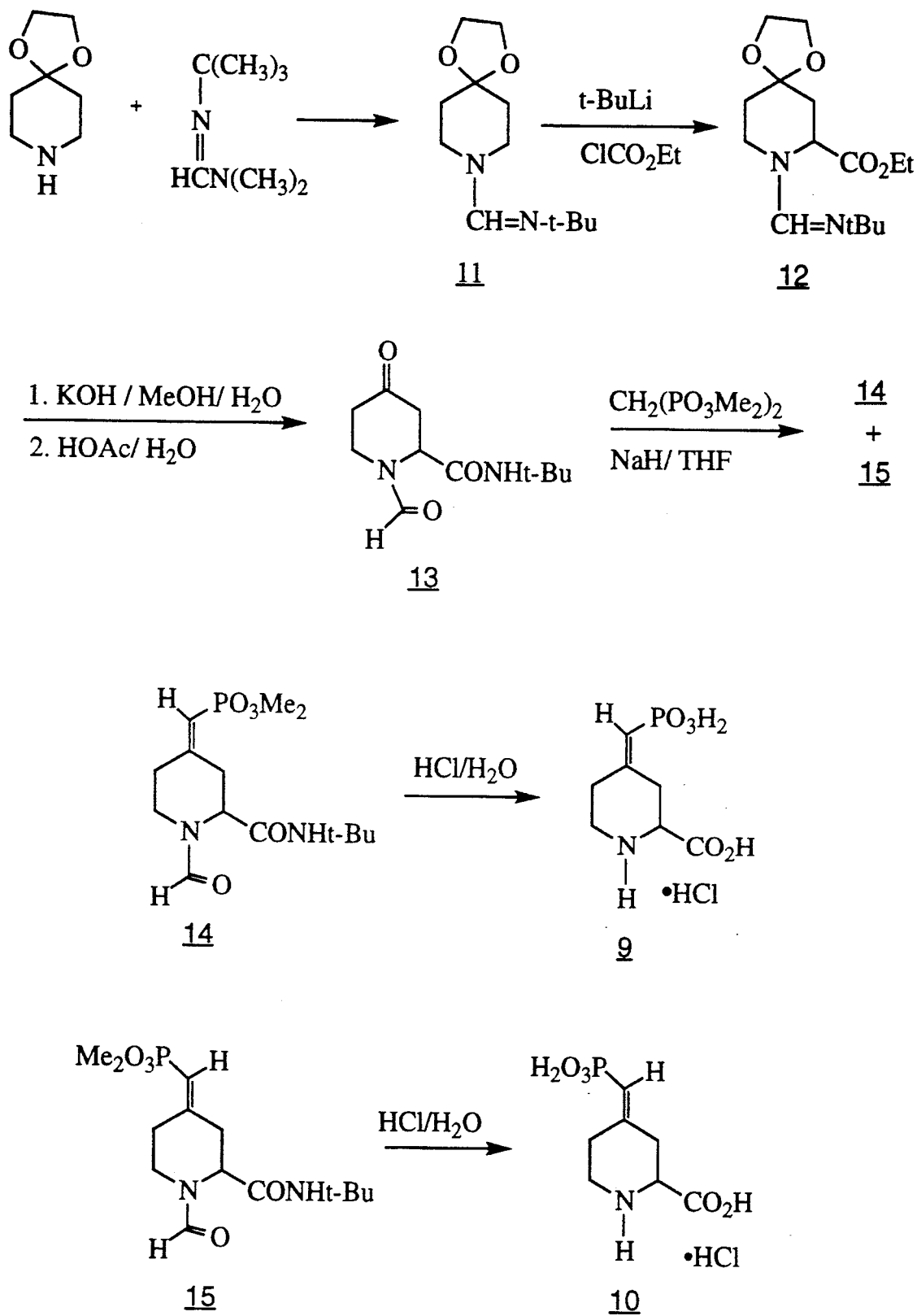
FIG. 2 is a reaction scheme for preparing compounds and salts of the invention as set out in Example 2.
Figure 3:
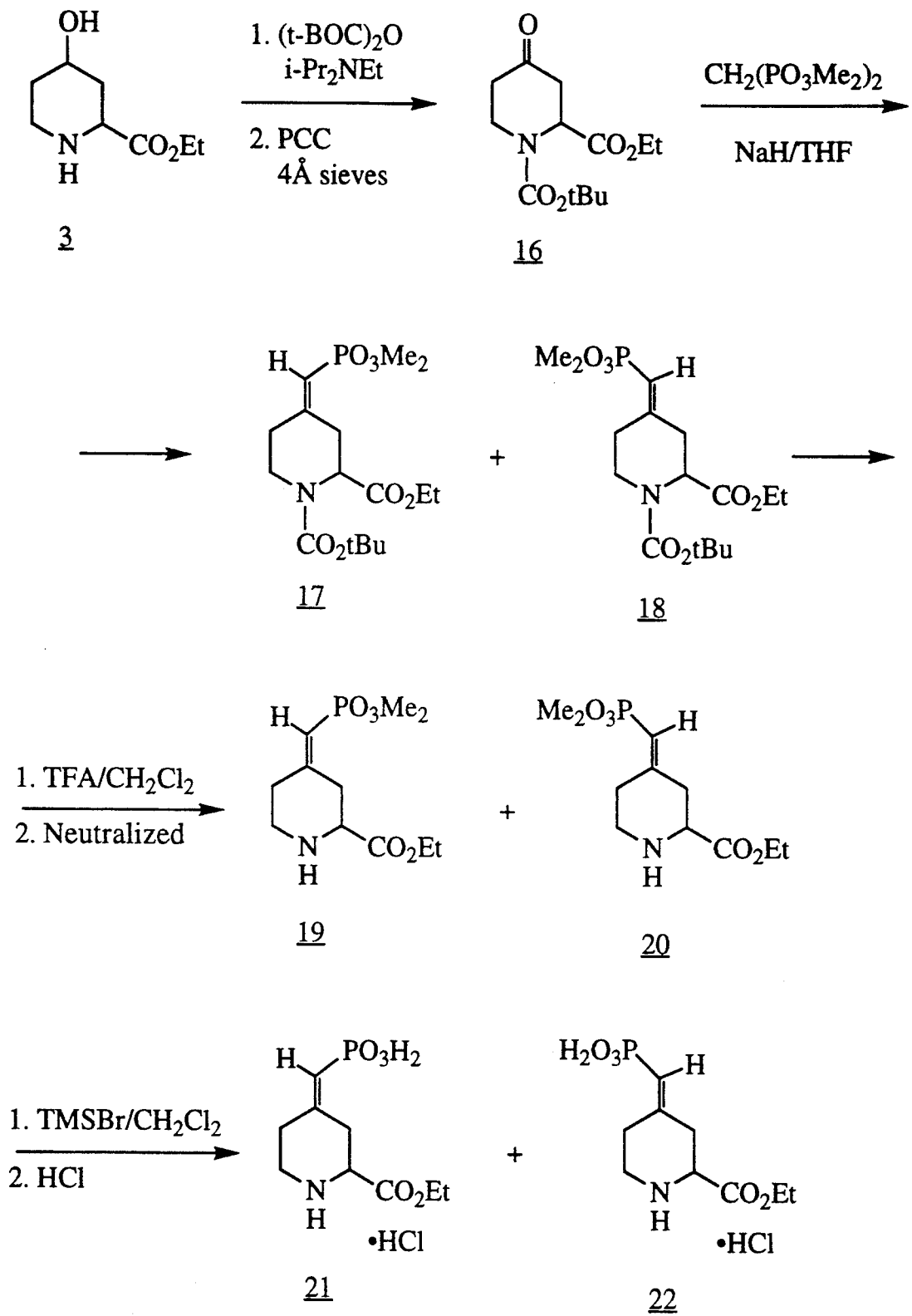
FIG. 3 is a reaction scheme for preparing compounds and salts of the invention as set out in Example 3.

The compounds of the invention can be prepared by three processes set forth in the Schemes 1-3, which are set forth in FIGS. 1-3 respectively.

The processes of Schemes 1, 2 and 3 are fully exemplified in Examples 1, 2 and 3. The schemes illustrate the preparation of both isomers of the "olefin" X group with free acid form at both the phosphonate and the carbonyl functionalities. In this process of Scheme 1, a suitably protected amine, protected carboxylic group ketone 6 is treated with tetramethyl methylene diphosphonate at moderate temperatures. This introduces the desired phosphonate group, as a dialkyl ester. Blocking groups can be removed and various $R_1$, $R_2$ and $R_3$ groups can be varied among H, and the various lower alkyls by hydrolysis and esterification reactions. Schemes 2 and 3 show variations on this general preparative process.

In Schemes 1, 2 and 3, n is generally shown as O. If one wants to have higher values i.e., 1, 2, 3, or 4) for n, and thus longer —$(CH_2)_n$— chain lengths, these can be attained. A suitably protected carbonyl such as 16 in Scheme 3 can be reacted with a triphenylphosphorane $Ph_3P=CH-(CH_2)_n-Z$, or a phosphorane ylide generated from $(EtO)_2P(O)-CH_2(CH_2)_n-Z$ wherein Z is a leaving group such as halo or a methoxy. These materials react in an inert solvent such as THF within a few hours at a moderate temperature to add the =CH—$(CH_2)_n$—Z group in place of the ketone oxygen. This yields a mixture of isomers which is beneficially separated at this point. The desired isomer is then treated with diethyl phosphate anion —$PO_3Et_2$ in an aprotic solvent such as DMF at moderate temperatures (50°-100° C.) for 2-12 hours. This allows the phosphate to displace the Z leaving group and give rise to the full range of n=1, 2, 3 or 4 groups depending upon the particular =CH$(CH_2)_n$—Z group employed. $R_1$, $R_2$ and $R_3$ can all be varied as previously described.

As shown in Schemes 1, 2 and 3, it is generally desirable to protect the various carbonyl and amine groups for these reactions. These protection-deprotection routes are known in the art.

=X can also be an

group, wherein $R_4$ is a halo instead of H. The $R_4$ halo can be present as a substituent in the phosphorane reagent, in the phosphonate reagent or the methylene of the tetramethylene diphosphonate reagent. This will insert the $R_4$ halo at the desired position.

In a final variation, =X can be =N—O—. This functionality can be introduced using well-known chemistry.

The reagents $H_2N-O-CH_2-PO_3H_2$ and $H_2N-O-(CH_2)_2-PO_3H_2$ are known and available as their HCl acid addition salts. Other equivalent materials, where n=2, 3 or 4, are preparable analogously. These reagents will react with a protected ketone such as 16 from Scheme 3 at a temperature of 0°-100° C., preferably from room temperature to 70° C. in, for example, an appropriate solvent such as water, alcohol, dioxane or THF. This will add the =N—O—$(CH_2)_n$—$PO_3H_3$ group in place of the ketone. Thereafter, the various protecting groups can be removed and the various hydrogens and alkyl groups substituted as $R_1$, $R_2$ and $R_3$ as noted above.

The pharmaceutically acceptable nontoxic salt derivatives of the compounds of Formula I are prepared by treating the free acids with an appropriate amount of pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, isopropanol, butanol, acetone, dioxane or tetrahydrofuran. The molar ratio of compounds of Formula I to base used are chosen to provide the ratio desired for any particular salt. For preparing, for example, the calcium salts or magnesium salts, the free acid starting material of Formula I can be treated with at least one-half molar equivalent of pharmaceutically acceptable base to yield a neutral salt. When the aluminum salts of the compounds of Formula I are prepared, at least one third molar equivalent of the pharmaceutically acceptable base are employed if a neutral salt product is desired.

The salt derivatives of the compounds of Formula I can be reconverted to their respective free acids by acidifying said salts with an acid, preferably an inorganic acid, e.g. hydrochloric acid, sulfuric acid, and the like, at temperature of from about 0° C. to about 50° C., preferably at room temperature.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, and under atmospheric or super-atmospheric pressure. The preferred solvents, catalysts and reaction conditions are set forth in the appended illustrative examples. The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

The following examples and illustrations are intended to illustrate the invention and are not to be construed as being limitations thereon. Reaction Schemes 1, 2 and 3 of FIGS. 1, 2 and 3 correspond to Examples 1, 2 and 3.

EXAMPLE 1

Synthesis of 4-(phosphonomethylidene)-2-piperidinecarboxylic acid (E-isomer and Z-isomer) (Scheme 1)

Commercially available 4-methoxypyridine N-oxide (50 g, 0.4 mol) was dissolved in dichloromethane (200 mL), and to it was added trimethylsilylcyanide (67.4 mL, 0.506 mol) at room temperature. Dimethylcarbamyl chloride (46.5 mL, 0.506 mol) was added dropwise with stirring to the reaction mixture over a 30-min period. The reaction mixture was stirred at room temperature for 24 hours. A solution of 10% aqueous potassium Carbonate (100 mL) was added dropwise, and stirring was continued for 15 minutes. The organic layer was separated, dried, and concentrated to afford 2-cyano-4-methoxypyridine 1 (51.5 g, 96%) as an off-white solid.

A solution of 2-cyano-4-methoxypyridine 1 (45 g, 0.34 mol) and 48% aqueous HBr (500 mL) was heated for 72 hours at reflux, then cooled to room temperature and concentrated in vacuo. To the residue was added anhydrous ethanol (1 L); then HCl gas was bubbled through the solution for 10 minutes. After heating overnight at reflux, the mixture was cooled to room temperature and concentrated to afford the desired ethyl ester 2 as a white solid (45.5 g, 80% yield).

This solid (10.1 g, 0.05 mol) was hydrogenated in ethanol/water (1:1, 100 mL) with $PtO_2$ (5 g) at 60 psi $H_2$ pressure at 60° C. for 18 hours. The reaction mixture was filtered through celite, and the filtrate was concentrated in vacuo to afford a crude solid 3 (9.68 g, 90%) as a white solid.

The ethyl ester 3 was dissolved in dichloromethane (150 mL)/anhydrous ethanol (75 mL) and to it was added diisopropylethylamine (15.65 mL) and a solution of di-tert-butyldicarbonate (19.64 g, 0.09 mol) in 180 mL of dichloromethane in four portions. The resultant mixture was stirred at room temperature for 18 h. The reaction mixture was filtered through celite and the filtrate evaporated to dryness at reduced pressure. The residue was dissolved in $CHCl_3$ and washed with 4% HCl. The organic phase was dried over $MgSO_4$ and evaporated to dryness at reduced pressure to afford 16.0 g of crude t-Boc-protected product. Purification by chromatography using 600 g flash chromatography silica gel and 30-50% EtOAc/hexane gave 10.01 g of pure t-Boc-N-protected piperidine derivative 4 (39% yield).

The N-protected ester 4 (6.1 g) was heated in 25 mL of t-butylamine at 140° C. for 18 h in a sealed tube to afford, after evaporation of the excess t-butylamine, the desired amide 5 $^1$H NMR ($CDCl_3$, 300 MHz): δ4.91 (m, 1H, 2-H), 4.20 (m, 2H, 6-$H_2$), 3.32 (m, 1H, 4-H), 1.72 [s, 9H, $C(CH_3)_3$], 1.51 [s, 9H, $C(CH_3)_3$] in an 85% yield. The alcohol 5 was then efficiently oxidized to the ketone with pyridinium chlorochromate (PCC). To a mixture of PCC (5.73 g, 0.027 mol), and 1.50 g powdered molecular sieves in 120 mL of $CH_2Cl_2$ (stirred for 1 h at room temperature, then cooled in an ice-water bath) was added dropwise over 30 min the alcohol 5 (3.32 g, 0.011 mol) in 30 mL of $CH_2Cl_2$. After stirring at room temperature for 3 h, the reaction mixture was suction-filtered directly through flash chromatography silica gel using $CH_2Cl_2$ to remove excess PCC. The reaction mixture was then chromatographed on 100 g of flash chromatography silica gel using 25% EtOAc/hexane to afford 1.48 g (46%) of ketone 6. $^1$H NMR ($CDCl_3$, 300 MHz): δ4.80 (m, 1H, 2-H), 1.51 [m, 9H, $C(CH_3)_3$], 1.32 [m, 9H, $C(CH_3)_3$]. HRMS for $C_{15}H_{26}NO_4$; Calcd. $M+H^+$ 299.1971. Found $M+H^+$ 299.1979.

A solution of ketone 6 (1.37 g, 0.0046 mol) in THF (50 mL) was added at −78° C. to the anion generated from NaH (0.387 g, 0.00968 mol) and tetramethyl methylenediphosphonate (2.247 g, 0.068 mol) in dry THF. The reaction mixture was then stirred at room temperature for 2.5 h. The THF was removed at reduced pressure water bath temperature below 30° C.) to afford 3.77 g of residue. The residue showed two spots by thin-layer chromatography. Purification using 65 g flash chromatography silica gel and developed in 75% EtOAc/hexane afforded 0.625 g (36%) of the cis-protected isomer 7 and 0.710 g (39%) of the trans-protected isomer 8. HRMS for 7 $C_{18}H_{33}N_2O_6P$. Calcd. $M+H^+$ 404.2154. Found $M+H^+$ 404.2174. $^1$H NMR ($CDCl_3$, 300 MHz) δ5.45 (d, 1H, J=16 Hz HC=C), 4.75 (m, 1H, H-2), 3.69-3.80 (m, 6H, $OCH_3$), 1.49 [s, 9H, $C(CH_3)_3$], 1.33 [s, 9H, $C(CH_3)_3$].

Indeed, it seems that the amide proton of the 2-CONHR is very important in the transition state complex in directing the orientation of the phosphonate. The ketone analog 6 with the N-Boc protecting group and the t-butyl amide functionality also results in an olefin product mixture that is much more readily chromatographed, resulting in a higher and purer yield of Z-isomer 7. Removal of the protecting group was then accomplished by refluxing the phosphonate 7 and 8 in 6N HCl for 18 h to afford 9 and 10 respectively in quantitative yield. 9: EIMS (m/e): 437 ($M.TMS_3^+$); $^1$H NMR (400 MHz, $D_2O$) δ3.80 (dd, J=4, 12 Hz, 1H $C_{2-H}$), 5.75 (d, J=16 Hz, 1H, HC=C) 10: EIMS (m/e) 437 ($M.TMS_3^+$); $^1$H NMR (400 MHz, $D_2O$) 3.86 dd, J=4,12 Hz, 1H, $C_{2H}$), 5.78 (d, J=16 Hz, 1H HC=C). NOESY on 10 showed an NOE between the vinylic proton at δ5.78 and $C-3H_3$ at δ2.8.

EXAMPLE 2

Synthesis of 4-(phosphonomethylidene)-2-piperidinecarboxylic acid (E-isomer and Z-isomer) (Scheme 2)

Treatment of 4-piperidine ethylene ketal (14 g) with N'-tert-butyl-N,N-dimethylformamidine (38 g) in toluene (100 mL) at 100° C. for 24 hours afforded the formamidine ketal 11, b.p. 87° C./0.15 mm, in 86% yield. A solution of the formamidine 11 (12 g) in ether (240 mL) was treated with t-butyllithium (1.5M, 42 mL) in pentane, and the anion was alkylated with ethyl chloroformate (6.6 mL). Aqueous workup and evaporation of the solvent afforded the ester 12 (90% yield). A solution of the ester 12 (9.8 g) in MeOH (12 mL) and 10% KOH in 50% $MeOH/H_2O$ (11 mL) was refluxed for 1.5 hours, cooled to room temperature, neutralized to pH 8 with 1M HCl, and evaporated to dryness. Flash column chromatography on silica gel using ethyl acetate as solvent afforded the ketal (3.3 g, 41% yield). IR ($CHCl_3$):3434 (N-H), 1674 cm$^{-1}$ (amide). EIMS (m/z): 270 ($M^+$). A solution of the ketal (3.2 g) in AcOH (28 mL) and $H_2O$ (28 mL) was heated at 80° C. for 2 hours, and the solvent was removed under reduced pressure. Crystallization from $CH_2Cl_2$—EtOAc yielded the ketone 13 (2.05 g, 75% yield). IR ($CHCl_3$): 3395 (N-H), 1725 (ketone), 1681 cm$^{-1}$ (amide). EIMS (m/z): 226 ($M^+$). A solution of ketone 13 (400 mg) in THF (20 mL) was added to the anion at −78° C., which was generated from NaH (98 mg) and tetramethyl methylenediphosphonate (0.90 g) in THF (12 mL). The bath was replaced with a water bath at room temperature, the mixture was stirred for 5 minutes, water was added (5 mL), and the solution was evaporated to dryness. Flash column chromatography on silica gel using CHCl$_3$/acetone (2:8) gave the exocyclic Z-isomer 14 (102 mg) in 17% yield and the exocyclic E-isomer 15 (150 mg) in 25% yield. The 14 was crystallized from EtOAc/hexane; IR (CHCl$_3$): 3342 (N-H), 1679 cm$^{-1}$ (amide). EIMS (m/z): 332 (M+).

NMR (CDCl$_3$, 90 MHz): $\delta$5.06 (dd, J=2 and 5 Hz, 1H, 2-H), 5.51 (d, J=16 Hz. 1H, HC=C). The exocyclic E-isomer 15 was crystallized from EtOAc/hexane; IR (CHCl$_3$): 3339 (N-H), 1678 cm$^{-1}$ (amide). EIMS (m/z): 332 (M+). NMR (CDCl$_3$, 90 MHz): $\delta$4.99 (dd, J=1 and 5 Hz, 1H, 2-H), 5.60 (d, J=16 Hz, 1H, HC=C).

The Z-isomer 14 (55 mg) was heated with 6N HCl/H$_2$O (3 mL) at 100° C. for 24 hours and evaporated to dryness. The residue was dissolved in MeOH (5 mL), treated with propylene oxide (0.5 mL), stirred for 0.5 hour, and evaporated to dryness. Purification by C$_{18}$ reverse-phase flash column chromatography, using water as solvent, gave compound 9 (52 mg, 70% yield). EIMS (m/z): 437 (M+ TMS$_3$+). NMR (D$_2$O, 400 MHz): $\delta$3.80 (dd, J=4 and 12 Hz, 1H, 2-H), 5.75 (d, J=16 Hz, 1H, HC=C).

The exocyclic E-isomer 15 (65 mg) was similarly treated with 6N HCl/H$_2$O (3 mL). After workup and purification, a compound 10 (75% yield) was obtained with about 10% of isomer 9 by NMR. EIMS (m/z): 437 (M+TMS$_3$+). NMR (D$_2$O, 400 MHz): $\delta$3.86 (dd, J=4 and 12 Hz, 1H, 2-H), 5.78 (d, J=16 Hz, 1H, HC=C). The 9 (Z-isomer) and 10 (E-isomer) were differentiated, and their structures were predicted on the basis of NOESY and decoupling experiments.

The NOESY experiment on 10 showed an NOE between the vinylic proton at $\delta$5.78 (d) and the 3H$_\beta$ at $\delta$2.8. The assignment of 3-H$_\beta$ was confirmed by decoupling the 2-H proton ($\delta$3.86), since the vicinal coupling of 3-H$_\beta$ to 2-H disappeared, leaving only the geminal coupling. Only the E-isomer would be expected to demonstrate this NOE between the vinylic proton and the 3-H, thus confirming that 10 is the E-isomer. In the case of the Z-isomer, there would be no coupling between the vinylic proton and 3-H$_\beta$. However, a NOESY experiment on 9 showed the NOE between the vinylic proton and a proton at C-5, but no effect on C-3, consistent with the Z-assignment for 9.

EXAMPLE 3

Synthesis of ethyl 4-(phosphonomethylidene)-2-piperidine carboxylate (E-isomer and Z-isomer) (Scheme 3)

The intermediate 3 from Scheme 1 was required for the synthesis of ethyl 4-(phosphonomethylidene)-2-piperidinecarboxylate. The crude residue 3 from Scheme 1 (9.6 g, 0.046 mol) was dissolved in CH$_2$Cl$_2$ (60 mL), anhydrous ethanol (30 mL), and diisopropylethylamine (8.01 mL). To this mixture was added di-tert-butyldicarbonate (9.5 g, 0.046 mol) in 5-mL portions every 10 minutes. The resultant mixture was stirred overnight at room temperature, then filtered through celite and concentrated in vacuo. The residue was extracted with ether-dichloromethane (2:1) and washed with 10% HCl. The organic layer was dried and evaporated to afford a light yellow clear liquid. The crude residue was purified by flash chromatography with EtOAc/hexane to afford the desired t-Boc-protected product (7.5 g, 60% yield). MS analysis showed the molecular ion peak at m/e 273. $^1$H NMR (90 MHz, CDCl$_3$): $\delta$4.70 (m, 1H), 4.19 (m, 3H), 3.84 (m, 1H), 3.38 (m, 2H), 2.43 (m, 1H), 2.12 (m, 1H), 1.90 (m, 1H), 1.69 (m, 1H), 1.46 (s, 9H), 1.27 (t, 3H). To a mixture of PCC (11.19 g, 0.05 mol), and 11.19 g of powdered molecular sieves, in 100 mL of dichloromethane (stirred for 1 hour at room temperature, then cooled in an ice-water bath) was added dropwise, over 30 minutes, alcohol (6.0 g, 0.022 mol) in dichloromethane (50 mL). After this solution was stirred for 3 hours at room temperature, 500 mL of ether was added and the mixture was filtered through a pad of celite (bottom) and a pad of silica gel in sintered glass funnels. The filtrate was concentrated in vacuo; then 150 mL of ether was added to the residue and the solution was filtered through silica gel. This filtrate was concentrated in vacuo to afford the desired ketone 16 as a yellow-green oil (5.70 g, 95% yield).

A solution of ketone 16 (4.3 g, 0.016 mol) in THF (60 mL) was added at −78° C. to the anion, which was generated from NaH (0.652 g, 0.027 mol) and tetramethyl methylene diphosphonate (6.31 g, 0.027 mol) in THF. The reaction mixture was stirred at room temperature for 1 hour. After that, water was added and the product extracted with chloroform. The chloroform layer was dried, filtered, and evaporated to afford a colorless viscous oil (4.5 g, 75%). The $^1$H NMR (400 MHz) clearly showed that the oil consisted of the E-isomer 18 (85%) and the Z-isomer 17 (15%). The Z-isomer and the E-isomer were differentiated and their structures predicted on the basis of NOESY and decoupling experiments. The NOESY experiment on this mixture showed an NOE between the vinylic proton and the 3-H$_\beta$. The assignment of 3-H$_\beta$ was confirmed by decoupling the 2-H, because the vicinal coupling of 3-H$_\beta$ to 2-H disappeared, leaving only the geminal coupling. The mixture of protected piperidine ester (17 and 18) (100 mg) was dissolved in dichloromethane (10 mL) and trifluoroacetic acid (10 mL). The reaction mixture was stirred at room temperature for 3 hours. After that the solvent was evaporated to afford an oil, which was triturated with ether. To the residue were added dichloromethane (50 mL) and saturated sodium bicarbonate solution; the organic layer was dried, filtered, and evaporated to give a mixture of deprotected ethylester ·19 and 20 as a thick oil (70 mg, 95% yield).

To the dichloromethane solution (10 mL) of the phosphonomethylidene ester 19 and 20 (138 mg, 0.5 mmol) was added bromotrimethylsilane (4 eq., 0.300 mL), and the mixture was stirred at room temperature for 3 hours. The solvent was evaporated, and methanol (2 mL) was added to hydrolyze the phosphonosilyl ester to give a residue. The residue was dissolved in a minimal amount of ethanol, and ether was added with HCl to give a light yellow powder. This powder was dissolved in ethanol, and propylene oxide (1 mL) was added to precipitate the mixture of phosphonic acid 21 and 22 (2:8 mixture) as a white powder (100 mg). EIMS (m/z): 393 (M+TMS$_2$)

$^1$H NMR (D$_2$O, 400 MHz): $\delta$1.28 (t, 3H, CH$_2$), 2.5 (m, 1H, 6-H$_\alpha$), 2.65 (bt, 1H, 3-H$_\alpha$), 2.95 (dd, 1H, 3-H$_\beta$), 3.12 (tt, 1H, 5-H$_\alpha$), 3.30 (dd, 1H, 6-H$_\beta$), 3.65 (bt, 1H, 5-H$_\beta$), 4.2 (dd, J=4 and 12 MHz, 1H, 2-H), 4.32 (q, 3H, CH$_3$), 5.80 (d, J=16 Hz, 1H, HC=C).

In Vitro Binding Assay using [³H]CGS-19755 as the Radioligand at the NMDA Receptor Site Compounds such as CGS-19755 (cis-4-(phosphonomethyl)-2-piperidinecarboxylic acid) have been shown to be high-affinity antagonists at the NMDA recognition site (Lehman et al., 1988; Murphy et al., 1987). The compounds of the invention were tested for their ability to inhibit [³H]CGS-19755 binding. Semipurified synaptic membranes were prepared according to the method of Bristow et al. (1986) with minor modifications. Adult male Sprague-Dawley rats were decapitated, and the forebrains were removed, weighed and homogenized in 20 volumes of 0.32M sucrose. The homogenate was centrifuged at 27,000×G for 15 minutes. The pellet was resuspended in 20 volumes of distilled water followed by centrifugation at 8000×G for minutes. Both the supernatant and the buffy coat layer, removed with 5 mM Tris-Cl (2 mL), pH 7.8, were pooled and centrifuged at 27,000×G for 15 minutes. The supernatant was removed and the pellet was covered with a small amount of 5 mM Tris-HCl and stored at −20° C. for least 18 hours. Membranes were then washed four times in 50 mM Tris-citrate, pH 7.1, and finally resuspended in the same buffer. This suspension was used for the binding assay immediately or frozen for subsequent use.

Aliquots of membranes (800 μl) were incubated with 10 nM [³H]CGS-19755 (100 μl) and varying concentrations of the test compounds (100 μl) for 15 minutes at 4° C. Then a filtration assay was used. The samples were filtered over glass fiber filters using a Brandel Cell Harvester. The filters were left overnight in 5 mL scintillation cocktail before counting.

Table 1 summarizes the results of the in vitro binding studies using [³H]CGS-19755 as the radioligand at the NMDA receptor site.

Ki values were calculated from the equation:

$$Ki = \frac{IC_{50}}{1 + \frac{[c]}{Kd}}$$

TABLE 1

In Vitro Binding Assay at the NMDA Receptor Site

| Compound | Ki (μM) [³H]CGS19755 |
|---|---|
| CGS-19755(cis-4-(phosphonomethyl)-2-piperidinecarboxylic acid) | 0.112 |
| E-4-(phosphonomethylidene)-2-piperidinecarboxylic acid | 0.59 |

In Vivo Protection in the Mouse Against NMDA-Induced Lethality

According to the method described by Ferkany et al. (1988), the test compounds were administered ip to four male Swiss-Webster mice (26–34 g) each, following 30 minutes later, 200 mg/kg of NMDA was administered to the mice each. The LD₅₀ of NMDA was found to be 164 mg/kg, and approximately 90% of the mice died at 200 mg/kg. Those compounds that protected three or more of the mice at any of the doses were evaluated further by determining the ED₅₀ values using three or more doses with the eight mice per dose. The ED₅₀ was estimated by the method of Litchfield and Wilcoxin (1949). Water-soluble compounds were dissolved in distilled water and administered in a volume of 10 mL/kg. Water-insoluble compounds were suspended in an aqueous solution of 0.5% methyl cellulose and administered in a volume of 20 mL/kg.

Table 2 also summarizes the results of this test.

TABLE 2

NMDA-Induced Lethality Test in the Mouse

| Compound | PD₅₀ (mg/kg) | Confidence Limits | Slope |
|---|---|---|---|
| CGS-19755 (cis-4-(phosphonomethyl)-2-piperidine-carboxylic acid) | 2.0 | 1.2–3.6 | 2.46 |
| E-4-(phosphonomethylidene-2-piperidine-carboxylic acid | 1.1 | 0.5–2.2 | 1.96 |

Representative Composition A

An oral suspension is prepared having the following composition

Ingredients

| | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Representative Composition B

| Ingredients | Quantity per tablet (mg) |
|---|---|
| active ingredient | 25 |
| cornstarch | 20 |
| lactose, spray-dried | 153 |
| magnesium stearate | 2 |

The above ingredients are thoroughly mixed and pressed into single-scored tablets.

EXAMPLES 0 and 4-1125

The reactions of Examples 1 and 2 and 3 are repeated varying the feedstocks as set forth in the preparation section. This gives rise to the following compounds of the invention:

| Example | X | n | R₁ | R₂ | R₃ |
|---|---|---|---|---|---|
| 1.2 | =C—H | 0 | H | H | H |
| 0 | =C—H | 0 | H | H | Methyl |
| 3 | =C—H | 0 | H | H | Ethyl |
| 4 | =C—H | 0 | H | H | Propyl |
| 5 | =C—H | 0 | H | H | Butyl |
| 6 | =C—H (with vertical bond) | 0 | H | Methyl | Methyl |

-continued

| Example | X | n | $R_1$ | $R_2$ | $R_3$ |
|---|---|---|---|---|---|
| 7 | =C−H | 0 | H | Methyl | Ethyl |
| 8 | =C−H | 0 | H | Methyl | Propyl |
| 9 | =C−H | 0 | H | Methyl | Butyl |
| 10 | =C−H | 0 | H | Ethyl | Ethyl |
| 11 | =C−H | 0 | H | Ethyl | Propyl |
| 12 | =C−H | 0 | H | Ethyl | Butyl |
| 13 | =C−H | 0 | H | Propyl | Propyl |
| 14 | =C−H | 0 | H | Propyl | Butyl |
| 15 | =C−H | 0 | H | Butyl | Butyl |
| 16 | =C−F | 0 | H | H | H |
| 17 | =C−F | 0 | H | H | Methyl |
| 18 | =C−F | 0 | H | H | Ethyl |
| 19 | =C−F | 0 | H | H | Propyl |
| 20 | =C−F | 0 | H | H | Butyl |
| 21 | =C−F | 0 | H | Methyl | Methyl |
| 22 | =C−F | 0 | H | Methyl | Ethyl |
| 23 | =C−F | 0 | H | Methyl | Propyl |
| 24 | =C−F | 0 | H | Methyl | Butyl |
| 25 | =C−F | 0 | H | Ethyl | Ethyl |
| 26 | =C−F | 0 | H | Ethyl | Propyl |
| 27 | =C−F | 0 | H | Ethyl | Butyl |
| 28 | =C−F | 0 | H | Propyl | Propyl |
| 29 | =C−F | 0 | H | Propyl | Butyl |

-continued

| Example | X | n | $R_1$ | $R_2$ | $R_3$ |
|---|---|---|---|---|---|
| 30 | =C(-F) | 0 | H | Butyl | Butyl |
| 31 | =N—O— | 0 | H | H | H |
| 32 | =N—O— | 0 | H | H | Methyl |
| 33 | =N—O— | 0 | H | H | Ethyl |
| 34 | =N—O— | 0 | H | H | Propyl |
| 35 | =N—O— | 0 | H | H | Butyl |
| 36 | =N—O— | 0 | H | Methyl | Methyl |
| 37 | =N—O— | 0 | H | Methyl | Ethyl |
| 38 | =N—O— | 0 | H | Methyl | Propyl |
| 39 | =N—O— | 0 | H | Methyl | Butyl |
| 40 | =N—O— | 0 | H | Ethyl | Ethyl |
| 41 | =N—O— | 0 | H | Ethyl | Propyl |
| 42 | =N—O— | 0 | H | Ethyl | Butyl |
| 43 | =N—O— | 0 | H | Propyl | Propyl |
| 44 | =N—O— | 0 | H | Propyl | Butyl |
| 45 | =N—O— | 0 | H | Butyl | Butyl |
| 46 | =C—H | 1 | H | H | H |
| 47 | =C—H | 1 | H | H | Methyl |
| 48 | =C—H | 1 | H | H | Ethyl |
| 49 | =C—H | 1 | H | H | Propyl |
| 50 | =C(-H) | 1 | H | H | Butyl |
| 51 | =C(-H) | 1 | H | Methyl | Methyl |
| 52 | =C(-H) | 1 | H | Methyl | Ethyl |
| 53 | =C—H | 1 | H | Methyl | Propyl |
| 54 | =C(-H) | 1 | H | Methyl | Butyl |
| 55 | =C(-H) | 1 | H | Ethyl | Ethyl |
| 56 | =C(-H) | 1 | H | Ethyl | Propyl |
| 57 | =C—H | 1 | H | Ethyl | Butyl |
| 58 | =C(-H) | 1 | H | Propyl | Propyl |
| 59 | =C(-H) | 1 | H | Propyl | Butyl |
| 60 | =C(-H) | 1 | H | Butyl | Butyl |
| 61 | =C(-F) | 1 | H | H | H |
| 62 | =C(-F) | 1 | H | H | Methyl |
| 63 | =C(-F) | 1 | H | H | Ethyl |
| 64 | =C(-F) | 1 | H | H | Propyl |
| 65 | =C(-F) | 1 | H | H | Butyl |

-continued

| Example | X | n | R₁ | R₂ | R₃ |
|---|---|---|---|---|---|
| 66 | =C−F | 1 | H | Methyl | Methyl |
| 67 | =C−F | 1 | H | Methyl | Ethyl |
| 68 | =C−F | 1 | H | Methyl | Propyl |
| 69 | =C−F | 1 | H | Methyl | Butyl |
| 70 | =C−F | 1 | H | Ethyl | Ethyl |
| 71 | =C−F | 1 | H | Ethyl | Propyl |
| 72 | =C−F | 1 | H | Ethyl | Butyl |
| 73 | =C−F | 1 | H | Propyl | Propyl |
| 74 | =C−F | 1 | H | Propyl | Butyl |
| 75 | =C−F | 1 | H | Butyl | Butyl |
| 76 | =N−O− | 1 | H | H | H |
| 77 | =N−O− | 1 | H | H | Methyl |
| 78 | =N−O− | 1 | H | H | Ethyl |
| 79 | =N−O− | 1 | H | H | Propyl |
| 80 | =N−O− | 1 | H | H | Butyl |
| 81 | =N−O− | 1 | H | Methyl | Methyl |
| 82 | =N−O− | 1 | H | Methyl | Ethyl |
| 83 | =N−O− | 1 | H | Methyl | Propyl |
| 84 | =N−O− | 1 | H | Methyl | Butyl |
| 85 | =N−O− | 1 | H | Ethyl | Ethyl |
| 86 | =N−O− | 1 | H | Ethyl | Propyl |
| 87 | =N−O− | 1 | H | Ethyl | Butyl |
| 88 | =N−O− | 1 | H | Propyl | Propyl |
| 89 | =N−O− | 1 | H | Propyl | Butyl |
| 90 | =N−O− | 1 | H | Butyl | Butyl |
| 91 | =C−H | 2 | H | H | H |
| 92 | =C−H | 2 | H | H | Methyl |
| 93 | =C−H | 2 | H | H | Ethyl |
| 94 | =C−H | 2 | H | H | Propyl |
| 95 | =C−H | 2 | H | H | Butyl |
| 96 | =C−H | 2 | H | Methyl | Methyl |
| 97 | =C−H | 2 | H | Methyl | Ethyl |
| 98 | =C−H | 2 | H | Methyl | Propyl |
| 99 | =C−H | 2 | H | Methyl | Butyl |

-continued

| Example | X | n | $R_1$ | $R_2$ | $R_3$ |
|---|---|---|---|---|---|
| 100 | $=\overset{\mid}{C}-H$ | 2 | H | Ethyl | Ethyl |
| 101 | $=\overset{\mid}{C}-H$ | 2 | H | Ethyl | Propyl |
| 102 | $=\overset{\mid}{C}-H$ | 2 | H | Ethyl | Butyl |
| 103 | $=\overset{\mid}{C}-H$ | 2 | H | Propyl | Propyl |
| 104 | $=\overset{\mid}{C}-H$ | 2 | H | Propyl | Butyl |
| 105 | $=\overset{\mid}{C}-H$ | 2 | H | Butyl | Butyl |
| 106 | $=\overset{\mid}{C}-F$ | 2 | H | H | H |
| 107 | $=\overset{\mid}{C}-F$ | 2 | H | H | Methyl |
| 108 | $=\overset{\mid}{C}-F$ | 2 | H | H | Ethyl |
| 109 | $=\overset{\mid}{C}-F$ | 2 | H | H | Propyl |
| 110 | $=\overset{\mid}{C}-F$ | 2 | H | H | Butyl |
| 111 | $=\overset{\mid}{C}-F$ | 2 | H | Methyl | Methyl |
| 112 | $=\overset{\mid}{C}-F$ | 2 | H | Methyl | Ethyl |
| 113 | $=\overset{\mid}{C}-F$ | 2 | H | Methyl | Propyl |
| 114 | $=\overset{\mid}{C}-F$ | 2 | H | Methyl | Butyl |
| 115 | $=\overset{\mid}{C}-F$ | 2 | H | Ethyl | Ethyl |
| 116 | $=\overset{\mid}{C}-F$ | 2 | H | Ethyl | Propyl |
| 117 | $=\overset{\mid}{C}-F$ | 2 | H | Ethyl | Butyl |
| 118 | $=\overset{\mid}{C}-F$ | 2 | H | Propyl | Propyl |
| 119 | $=\overset{\mid}{C}-F$ | 2 | H | Propyl | Butyl |
| 120 | $=\overset{\mid}{C}-F$ | 2 | H | Butyl | Butyl |
| 121 | =N—O— | 2 | H | H | H |
| 122 | =N—O— | 2 | H | H | Methyl |
| 123 | =N—O— | 2 | H | H | Ethyl |
| 124 | =N—O— | 2 | H | H | Propyl |
| 125 | =N—O— | 2 | H | H | Butyl |
| 126 | =N—O— | 2 | H | Methyl | Methyl |

-continued

| Example | X | n | $R_1$ | $R_2$ | $R_3$ |
|---|---|---|---|---|---|
| 127 | =N—O— | 2 | H | Methyl | Ethyl |
| 128 | =N—O— | 2 | H | Methyl | Propyl |
| 129 | =N—O— | 2 | H | Methyl | Butyl |
| 130 | =N—O— | 2 | H | Ethyl | Ethyl |
| 131 | =N—O— | 2 | H | Ethyl | Propyl |
| 132 | =N—O— | 2 | H | Ethyl | Butyl |
| 133 | =N—O— | 2 | H | Propyl | Propyl |
| 134 | =N—O— | 2 | H | Propyl | Butyl |
| 135 | =N—O— | 2 | H | Butyl | Butyl |
| 136 | =C—H | 3 | H | H | H |
| 137 | =C—H | 3 | H | H | Methyl |
| 138 | =C—H | 3 | H | H | Ethyl |
| 139 | =C—H | 3 | H | H | Propyl |
| 140 | =C—H | 3 | H | H | Butyl |
| 141 | =C—H | 3 | H | Methyl | Methyl |
| 142 | =C—H | 3 | H | Methyl | Ethyl |
| 143 | =C—H | 3 | H | Methyl | Propyl |
| 144 | =C—H | 3 | H | Methyl | Butyl |
| 145 | =C—H | 3 | H | Ethyl | Ethyl |
| 146 | =C—H | 3 | H | Ethyl | Propyl |
| 147 | =C—H | 3 | H | Ethyl | Butyl |
| 148 | =C—H | 3 | H | Propyl | Propyl |
| 149 | =C—H | 3 | H | Propyl | Butyl |
| 150 | =C—H | 3 | H | Butyl | Butyl |
| 151 | =C—F | 3 | H | H | H |
| 152 | =C—F | 3 | H | H | Methyl |
| 153 | =C—F | 3 | H | H | Ethyl |
| 154 | =C—F | 3 | H | H | Propyl |
| 155 | =C—F | 3 | H | H | Butyl |
| 156 | =C—F | 3 | H | Methyl | Methyl |
| 157 | =C—F | 3 | H | Methyl | Ethyl |

-continued

| Example | X | n | $R_1$ | $R_2$ | $R_3$ |
|---|---|---|---|---|---|
| 158 | $=\overset{\mid}{C}-F$ | 3 | H | Methyl | Propyl |
| 159 | $=\overset{\mid}{C}-F$ | 3 | H | Methyl | Butyl |
| 160 | $=\overset{\mid}{C}-F$ | 3 | H | Ethyl | Ethyl |
| 161 | $=\overset{\mid}{C}-F$ | 3 | H | Ethyl | Propyl |
| 162 | $=\overset{\mid}{C}-F$ | 3 | H | Ethyl | Butyl |
| 163 | $=\overset{\mid}{C}-F$ | 3 | H | Propyl | Propyl |
| 164 | $=\overset{\mid}{C}-F$ | 3 | H | Propyl | Butyl |
| 165 | $=\overset{\mid}{C}-F$ | 3 | H | Butyl | Butyl |
| 166 | =N—O— | 3 | H | H | H |
| 167 | =N—O— | 3 | H | H | Methyl |
| 168 | =N—O— | 3 | H | H | Ethyl |
| 169 | =N—O— | 3 | H | H | Propyl |
| 170 | =N—O— | 3 | H | H | Butyl |
| 171 | =N—O— | 3 | H | Methyl | Methyl |
| 172 | =N—O— | 3 | H | Methyl | Ethyl |
| 173 | =N—O— | 3 | H | Methyl | Propyl |
| 174 | =N—O— | 3 | H | Methyl | Butyl |
| 175 | =N—O— | 3 | H | Ethyl | Ethyl |
| 176 | =N—O— | 3 | H | Ethyl | Propyl |
| 177 | =N—O— | 3 | H | Ethyl | Butyl |
| 178 | =N—O— | 3 | H | Propyl | Propyl |
| 179 | =N—O— | 3 | H | Propyl | Butyl |
| 180 | =N—O— | 3 | H | Butyl | Butyl |
| 181 | =C—H | 4 | H | H | H |
| 182 | $=\overset{\mid}{C}-H$ | 4 | H | H | Methyl |
| 183 | $=\overset{\mid}{C}-H$ | 4 | H | H | Ethyl |
| 184 | =C—H | 4 | H | H | Propyl |
| 185 | $=\overset{\mid}{C}-H$ | 4 | H | H | Butyl |
| 186 | $=\overset{\mid}{C}-H$ | 4 | H | Methyl | Methyl |
| 187 | $=\overset{\mid}{C}-H$ | 4 | H | Methyl | Ethyl |
| 188 | $=\overset{\mid}{C}-H$ | 4 | H | Methyl | Propyl |
| 189 | $=\overset{\mid}{C}-H$ | 4 | H | Methyl | Butyl |
| 190 | $=\overset{\mid}{C}-H$ | 4 | H | Ethyl | Ethyl |

-continued

| Example | X | n | $R_1$ | $R_2$ | $R_3$ |
|---|---|---|---|---|---|
| 191 | =C(-H)- | 4 | H | Ethyl | Propyl |
| 192 | =C(-H)- | 4 | H | Ethyl | Butyl |
| 193 | =C(-H)- | 4 | H | Propyl | Propyl |
| 194 | =C(-H)- | 4 | H | Propyl | Butyl |
| 195 | =C(-H)- | 4 | H | Butyl | Butyl |
| 196 | =C(-F)- | 4 | H | H | H |
| 197 | =C(-F)- | 4 | H | H | Methyl |
| 198 | =C(-F)- | 4 | H | H | Ethyl |
| 199 | =C(-F)- | 4 | H | H | Propyl |
| 200 | =C(-F)- | 4 | H | H | Butyl |
| 201 | =C(-F)- | 4 | H | Methyl | Methyl |
| 202 | =C(-F)- | 4 | H | Methyl | Ethyl |
| 203 | =C(-F)- | 4 | H | Methyl | Propyl |
| 204 | =C(-F)- | 4 | H | Methyl | Butyl |
| 205 | =C(-F)- | 4 | H | Ethyl | Ethyl |
| 206 | =C(-F)- | 4 | H | Ethyl | Propyl |
| 207 | =C(-F)- | 4 | H | Ethyl | Butyl |
| 208 | =C(-F)- | 4 | H | Propyl | Propyl |
| 209 | =C(-F)- | 4 | H | Propyl | Butyl |
| 210 | =C(-F)- | 4 | H | Butyl | Butyl |
| 211 | =N—O— | 4 | H | H | H |
| 212 | =N—O— | 4 | H | H | Methyl |
| 213 | =N—O— | 4 | H | H | Ethyl |
| 214 | =N—O— | 4 | H | H | Propyl |
| 215 | =N—O— | 4 | H | H | Butyl |

-continued

| Example | X | n | R₁ | R₂ | R₃ |
|---|---|---|---|---|---|
| 216 | =N—O— | 4 | H | Methyl | Methyl |
| 217 | =N—O— | 4 | H | Methyl | Ethyl |
| 218 | =N—O— | 4 | H | Methyl | Propyl |
| 219 | =N—O— | 4 | H | Methyl | Butyl |
| 220 | =N—O— | 4 | H | Ethyl | Ethyl |
| 221 | =N—O— | 4 | H | Ethyl | Propyl |
| 222 | =N—O— | 4 | H | Ethyl | Butyl |
| 223 | =N—O— | 4 | H | Propyl | Propyl |
| 224 | =N—O— | 4 | H | Propyl | Butyl |
| 225 | =N—O— | 4 | H | Butyl | Butyl |
| 226 | =C—H | 0 | Methyl | H | H |
| 227 | =C—H | 0 | Methyl | H | Methyl |
| 228 | =C—H | 0 | Methyl | H | Ethyl |
| 229 | =C—H | 0 | Methyl | H | Propyl |
| 230 | =C—H | 0 | Methyl | H | Butyl |
| 231 | =C—H— | 0 | Methyl | Methyl | Methyl |
| 232 | =C—H | 0 | Methyl | Methyl | Ethyl |
| 233 | =C—H | 0 | Methyl | Methyl | Propyl |
| 234 | =C—H— | 0 | Methyl | Methyl | Butyl |
| 235 | =C—H— | 0 | Methyl | Ethyl | Ethyl |
| 236 | =C—H | 0 | Methyl | Ethyl | Propyl |
| 237 | =C—H | 0 | Methyl | Ethyl | Butyl |
| 238 | =C—H | 0 | Methyl | Propyl | Propyl |
| 239 | =C—H | 0 | Methyl | Propyl | Butyl |
| 240 | =C—H | 0 | Methyl | Butyl | Butyl |
| 241 | =C—F | 0 | Methyl | H | H |
| 242 | =C—F | 0 | Methyl | H | Methyl |
| 243 | =C—F | 0 | Methyl | H | Ethyl |
| 244 | =C—F | 0 | Methyl | H | Propyl |
| 245 | =C—F | 0 | Methyl | H | Butyl |
| 246 | =C—F | 0 | Methyl | Methyl | Methyl |
| 247 | =C—F | 0 | Methyl | Methyl | Ethyl |
| 248 | =C—F | 0 | Methyl | Methyl | Propyl |
| 249 | =C—F | 0 | Methyl | Methyl | Butyl |

-continued

| Example | X | n | R₁ | R₂ | R₃ |
|---|---|---|---|---|---|
| 250 | =C(−F) | 0 | Methyl | Ethyl | Ethyl |
| 251 | =C(−F) | 0 | Methyl | Ethyl | Propyl |
| 252 | =C(−F) | 0 | Methyl | Ethyl | Butyl |
| 253 | =C(−F) | 0 | Methyl | Propyl | Propyl |
| 254 | =C(−F) | 0 | Methyl | Propyl | Butyl |
| 255 | =C(−F) | 0 | Methyl | Butyl | Butyl |
| 256 | =C(−H) | 0 | Ethyl | H | H |
| 257 | =C(−H) | 0 | Ethyl | H | Methyl |
| 258 | =C(−H) | 0 | Ethyl | H | Ethyl |
| 259 | =C(−H) | 0 | Ethyl | H | Propyl |
| 260 | =C(−H) | 0 | Ethyl | H | Butyl |
| 261 | =C(−H) | 0 | Ethyl | Methyl | Methyl |
| 262 | =C−H− | 0 | Ethyl | Methyl | Ethyl |
| 263 | =C(−H) | 0 | Ethyl | Methyl | Propyl |
| 264 | =C(−H) | 0 | Ethyl | Methyl | Butyl |
| 265 | =C(−H) | 0 | Ethyl | Ethyl | Ethyl |
| 266 | =C(−H) | 0 | Ethyl | Ethyl | Propyl |
| 267 | =C(−H) | 0 | Ethyl | Ethyl | Butyl |
| 268 | =C(−H) | 0 | Ethyl | Propyl | Propyl |
| 269 | =C(−H) | 0 | Ethyl | Propyl | Butyl |
| 270 | =C(−H) | 0 | Ethyl | Butyl | Butyl |
| 271 | =C−F | 0 | Ethyl | H | H |
| 272 | =C−F | 0 | Ethyl | H | Methyl |
| 273 | =C−F | 0 | Ethyl | H | Ethyl |

-continued

| Example | X | n | $R_1$ | $R_2$ | $R_3$ |
|---|---|---|---|---|---|
| 274 | $=\overset{\vert}{C}-F$ | 0 | Ethyl | H | Propyl |
| 275 | $=\overset{\vert}{C}-F$ | 0 | Ethyl | H | Butyl |
| 276 | $=\overset{\vert}{C}-F$ | 0 | Ethyl | Methyl | Methyl |
| 277 | $=\overset{\vert}{C}-F$ | 0 | Ethyl | Methyl | Ethyl |
| 278 | $=\overset{\vert}{C}-F$ | 0 | Ethyl | Methyl | Propyl |
| 279 | $=\overset{\vert}{C}-F$ | 0 | Ethyl | Methyl | Butyl |
| 280 | $=\overset{\vert}{C}-F$ | 0 | Ethyl | Ethyl | Ethyl |
| 281 | $=\overset{\vert}{C}-F$ | 0 | Ethyl | Ethyl | Propyl |
| 282 | $=\overset{\vert}{C}-F$ | 0 | Ethyl | Ethyl | Butyl |
| 283 | $=\overset{\vert}{C}-F$ | 0 | Ethyl | Propyl | Propyl |
| 284 | $=\overset{\vert}{C}-F$ | 0 | Ethyl | Propyl | Butyl |
| 285 | $=C-F$ | 0 | Ethyl | Butyl | Butyl |
| 286 | $=C-H$ | 0 | Propyl | H | H |
| 287 | $=\overset{\vert}{C}-H$ | 0 | Propyl | H | Methyl |
| 288 | $=\overset{\vert}{C}-H$ | 0 | Propyl | H | Ethyl |
| 289 | $=\overset{\vert}{C}-H$ | 0 | Propyl | H | Propyl |
| 290 | $=\overset{\vert}{C}-H$ | 0 | Propyl | H | Butyl |
| 291 | $=\overset{\vert}{C}-H$ | 0 | Propyl | Methyl | Methyl |
| 292 | $=\overset{\vert}{C}-H$ | 0 | Propyl | Methyl | Ethyl |
| 293 | $=\overset{\vert}{C}-H$ | 0 | Propyl | Methyl | Propyl |
| 294 | $=\overset{\vert}{C}-H$ | 0 | Propyl | Methyl | Butyl |
| 295 | $=\overset{\vert}{C}-H$ | 0 | Propyl | Ethyl | Ethyl |

-continued

| Example | X | n | R₁ | R₂ | R₃ |
|---|---|---|---|---|---|
| 296 | =C—H | 0 | Propyl | Ethyl | Propyl |
| 297 | =C—H | 0 | Propyl | Ethyl | Butyl |
| 298 | =C—H | 0 | Propyl | Propyl | Propyl |
| 299 | =C—H | 0 | Propyl | Propyl | Butyl |
| 300 | =C—H | 0 | Propyl | Butyl | Butyl |
| 301 | =C—F | 0 | Propyl | H | H |
| 302 | =C—F | 0 | Propyl | H | Methyl |
| 303 | =C—F | 0 | Propyl | H | Ethyl |
| 304 | =C—F | 0 | Propyl | H | Propyl |
| 305 | =C—F | 0 | Propyl | H | Butyl |
| 306 | =C—F | 0 | Propyl | Methyl | Methyl |
| 307 | =C—F | 0 | Propyl | Methyl | Ethyl |
| 308 | =C—F | 0 | Propyl | Methyl | Propyl |
| 309 | =C—F | 0 | Propyl | Methyl | Butyl |
| 310 | =C—F | 0 | Propyl | Ethyl | Ethyl |
| 311 | =C—F | 0 | Propyl | Ethyl | Propyl |
| 312 | =C—F | 0 | Propyl | Ethyl | Butyl |
| 313 | =C—F | 0 | Propyl | Propyl | Propyl |
| 314 | =C—F | 0 | Propyl | Propyl | Butyl |
| 315 | =C—F | 0 | Propyl | Butyl | Butyl |
| 316 | =C—H | 0 | Butyl | H | H |
| 317 | =C—H | 0 | Butyl | H | Methyl |
| 318 | =C—H | 0 | Butyl | H | Ethyl |
| 319 | =C—H | 0 | Butyl | H | Propyl |
| 320 | =C—H | 0 | Butyl | H | Butyl |
| 321 | =C—H | 0 | Butyl | Methyl | Methyl |

-continued

| Example | X | n | R₁ | R₂ | R₃ |
|---------|---|---|----|----|----|
| 322 | =C(-H) | 0 | Butyl | Methyl | Ethyl |
| 323 | =C(-H) | 0 | Butyl | Methyl | Propyl |
| 324 | =C(-H) | 0 | Butyl | Methyl | Butyl |
| 325 | =C(-H) | 0 | Butyl | Ethyl | Ethyl |
| 326 | =C(-H) | 0 | Butyl | Ethyl | Propyl |
| 327 | =C(-H) | 0 | Butyl | Ethyl | Butyl |
| 328 | =C(-H) | 0 | Butyl | Propyl | Propyl |
| 329 | =C(-H) | 0 | Butyl | Propyl | Butyl |
| 330 | =C(-H) | 0 | Butyl | Butyl | Butyl |
| 331 | =C(-F) | 0 | Butyl | H | H |
| 332 | =C(-F) | 0 | Butyl | H | Methyl |
| 333 | =C(-F) | 0 | Butyl | H | Ethyl |
| 334 | =C(-F) | 0 | Butyl | H | Propyl |
| 335 | =C(-F) | 0 | Butyl | H | Butyl |
| 336 | =C(-F) | 0 | Butyl | Methyl | Methyl |
| 337 | =C(-F) | 0 | Butyl | Methyl | Ethyl |
| 338 | =C(-F) | 0 | Butyl | Methyl | Propyl |
| 339 | =C(-F) | 0 | Butyl | Methyl | Butyl |
| 340 | =C(-F) | 0 | Butyl | Ethyl | Ethyl |
| 341 | =C(-F) | 0 | Butyl | Ethyl | Propyl |
| 342 | =C(-F) | 0 | Butyl | Ethyl | Butyl |

-continued

| Example | X | n | R₁ | R₂ | R₃ |
|---|---|---|---|---|---|
| 343 | $=\overset{\vert}{C}-F$ | 0 | Butyl | Propyl | Propyl |
| 344 | $=\overset{\vert}{C}-F$ | 0 | Butyl | Propyl | Butyl |
| 345 | $=\overset{\vert}{C}-F$ | 0 | Butyl | Butyl | Butyl |
| 346 | $=\overset{\vert}{C}-H$ | 1 | Methyl | H | H |
| 347 | $=\overset{\vert}{C}-H$ | 1 | Methyl | H | Methyl |
| 348 | $=\overset{\vert}{C}-H$ | 1 | Methyl | H | Ethyl |
| 349 | $=\overset{\vert}{C}-H$ | 1 | Methyl | H | Propyl |
| 350 | $=\overset{\vert}{C}-H$ | 1 | Methyl | H | Butyl |
| 351 | $=\overset{\vert}{C}-H$ | 1 | Methyl | Methyl | Methyl |
| 352 | $=\overset{\vert}{C}-H$ | 1 | Methyl | Methyl | Ethyl |
| 353 | $=\overset{\vert}{C}-H$ | 1 | Methyl | Methyl | Propyl |
| 354 | $=\overset{\vert}{C}-H$ | 1 | Methyl | Methyl | Butyl |
| 355 | $=\overset{\vert}{C}-H$ | 1 | Methyl | Ethyl | Ethyl |
| 356 | $=\overset{\vert}{C}-H$ | 1 | Methyl | Ethyl | Propyl |
| 357 | $=\overset{\vert}{C}-H$ | 1 | Methyl | Ethyl | Butyl |
| 358 | $=\overset{\vert}{C}-H$ | 1 | Methyl | Propyl | Propyl |
| 359 | $=\overset{\vert}{C}-H$ | 1 | Methyl | Propyl | Butyl |
| 360 | $=\overset{\vert}{C}-H$ | 1 | Methyl | Butyl | Butyl |
| 361 | =C—F | 1 | Methyl | H | H |
| 362 | =C—F | 1 | Methyl | H | Methyl |
| 363 | =C—F | 1 | Methyl | H | Ethyl |
| 364 | =C—F | 1 | Methyl | H | Propyl |
| 365 | =C—F | 1 | Methyl | H | Butyl |
| 366 | $=\overset{\vert}{C}-F$ | 1 | Methyl | Methyl | Methyl |
| 367 | =C—F | 1 | Methyl | Methyl | Ethyl |
| 368 | =C—F | 1 | Methyl | Methyl | Propyl |
| 369 | =C—F | 1 | Methyl | Methyl | Butyl |

-continued

| Example | X | n | $R_1$ | $R_2$ | $R_3$ |
|---|---|---|---|---|---|
| 370 | =C-F | 1 | Methyl | Ethyl | Ethyl |
| 371 | =C-F | 1 | Methyl | Ethyl | Propyl |
| 372 | =C-F | 1 | Methyl | Ethyl | Butyl |
| 373 | =C-F | 1 | Methyl | Propyl | Propyl |
| 374 | =C-F | 1 | Methyl | Propyl | Butyl |
| 375 | =C-F | 1 | Methyl | Butyl | Butyl |
| 376 | =C-H | 1 | Ethyl | H | H |
| 377 | =C-H | 1 | Ethyl | H | Methyl |
| 378 | =C-H | 1 | Ethyl | H | Ethyl |
| 379 | =C-H | 1 | Ethyl | H | Propyl |
| 380 | =C-H | 1 | Ethyl | H | Butyl |
| 381 | =C-H | 1 | Ethyl | Methyl | Methyl |
| 382 | =C-H | 1 | Ethyl | Methyl | Ethyl |
| 383 | =C-H | 1 | Ethyl | Methyl | Propyl |
| 384 | =C-H | 1 | Ethyl | Methyl | Butyl |
| 385 | =C-H | 1 | Ethyl | Ethyl | Ethyl |
| 386 | =C-H | 1 | Ethyl | Ethyl | Propyl |
| 387 | =C-H | 1 | Ethyl | Ethyl | Butyl |
| 388 | =C-H | 1 | Ethyl | Propyl | Propyl |
| 389 | =C-H | 1 | Ethyl | Propyl | Butyl |
| 390 | =C-H | 1 | Ethyl | Butyl | Butyl |

-continued

| Example | X | n | R₁ | R₂ | R₃ |
|---|---|---|---|---|---|
| 391 | =C−F | 1 | Ethyl | H | H |
| 392 | =C−F | 1 | Ethyl | H | Methyl |
| 393 | =C−F | 1 | Ethyl | H | Ethyl |
| 394 | =C−F | 1 | Ethyl | H | Propyl |
| 395 | =C−F | 1 | Ethyl | H | Butyl |
| 396 | =C−F | 1 | Ethyl | Methyl | Methyl |
| 397 | =C−F | 1 | Ethyl | Methyl | Ethyl |
| 398 | =C−F | 1 | Ethyl | Methyl | Propyl |
| 399 | =C−F | 1 | Ethyl | Methyl | Butyl |
| 400 | =C−F | 1 | Ethyl | Ethyl | Ethyl |
| 401 | =C−F | 1 | Ethyl | Ethyl | Propyl |
| 402 | =C−F | 1 | Ethyl | Ethyl | Butyl |
| 403 | =C−F | 1 | Ethyl | Propyl | Propyl |
| 404 | =C−F | 1 | Ethyl | Propyl | Butyl |
| 405 | =C−F | 1 | Ethyl | Butyl | Butyl |
| 406 | =C−H | 1 | Propyl | H | H |
| 407 | =C−H | 1 | Propyl | H | Methyl |
| 408 | =C−H | 1 | Propyl | H | Ethyl |
| 409 | =C−H | 1 | Propyl | H | Propyl |
| 410 | =C−H | 1 | Propyl | H | Butyl |
| 411 | =C−H | 1 | Propyl | Methyl | Methyl |
| 412 | =C−H | 1 | Propyl | Methyl | Ethyl |
| 413 | =C−H | 1 | Propyl | Methyl | Propyl |
| 414 | =C−H | 1 | Propyl | Methyl | Butyl |
| 415 | =C−H | 1 | Propyl | Ethyl | Ethyl |

-continued

| Example | X | n | R₁ | R₂ | R₃ |
|---|---|---|---|---|---|
| 416 | =C(-H)- | 1 | Propyl | Ethyl | Propyl |
| 417 | =C(-H)- | 1 | Propyl | Ethyl | Butyl |
| 418 | =C(-H)- | 1 | Propyl | Propyl | Propyl |
| 419 | =C(-H)- | 1 | Propyl | Propyl | Butyl |
| 420 | =C(-H)- | 1 | Propyl | Butyl | Butyl |
| 421 | =C(-F)- | 1 | Propyl | H | H |
| 422 | =C(-F)- | 1 | Propyl | H | Methyl |
| 423 | =C(-F)- | 1 | Propyl | H | Ethyl |
| 424 | =C(-F)- | 1 | Propyl | H | Propyl |
| 425 | =C(-F)- | 1 | Propyl | H | Butyl |
| 426 | =C-F | 1 | Propyl | Methyl | Methyl |
| 427 | =C(-F)- | 1 | Propyl | Methyl | Ethyl |
| 428 | =C(-F)- | 1 | Propyl | Methyl | Propyl |
| 429 | =C(-F)- | 1 | Propyl | Methyl | Butyl |
| 430 | =C(-F)- | 1 | Propyl | Ethyl | Ethyl |
| 431 | =C(-F)- | 1 | Propyl | Ethyl | Propyl |
| 432 | =C(-F)- | 1 | Propyl | Ethyl | Butyl |
| 433 | =C(-F)- | 1 | Propyl | Propyl | Propyl |
| 434 | =C(-F)- | 1 | Propyl | Propyl | Butyl |
| 435 | =C(-F)- | 1 | Propyl | Butyl | Butyl |
| 436 | =C(-H)- | 1 | Butyl | H | H |
| 437 | =C(-H)- | 1 | Butyl | H | Methyl |

-continued

| Example | X | n | R₁ | R₂ | R₃ |
|---|---|---|---|---|---|
| 438 | =C−H | 1 | Butyl | H | Ethyl |
| 439 | =C−H | 1 | Butyl | H | Propyl |
| 440 | =C−H | 1 | Butyl | H | Butyl |
| 441 | =C−H | 1 | Butyl | Methyl | Methyl |
| 442 | =C−H | 1 | Butyl | Methyl | Ethyl |
| 443 | =C−H | 1 | Butyl | Methyl | Propyl |
| 444 | =C−H | 1 | Butyl | Methyl | Butyl |
| 445 | =C−H | 1 | Butyl | Ethyl | Ethyl |
| 446 | =C−H | 1 | Butyl | Ethyl | Propyl |
| 447 | =C−H | 1 | Butyl | Ethyl | Butyl |
| 448 | =C−H | 1 | Butyl | Propyl | Propyl |
| 449 | =C−H | 1 | Butyl | Propyl | Butyl |
| 450 | =C−H | 1 | Butyl | Butyl | Butyl |
| 451 | =C−F | 1 | Butyl | H | H |
| 452 | =C−F | 1 | Butyl | H | Methyl |
| 453 | =C−F | 1 | Butyl | H | Ethyl |
| 454 | =C−F | 1 | Butyl | H | Propyl |
| 455 | =C−F | 1 | Butyl | H | Butyl |
| 456 | =C−F | 1 | Butyl | Methyl | Methyl |
| 457 | =C−F | 1 | Butyl | Methyl | Ethyl |
| 458 | =C−F | 1 | Butyl | Methyl | Propyl |
| 459 | =C−F | 1 | Butyl | Methyl | Butyl |
| 460 | =C−F | 1 | Butyl | Ethyl | Ethyl |

-continued

| Example | X | n | $R_1$ | $R_2$ | $R_3$ |
| --- | --- | --- | --- | --- | --- |
| 461 | $=\overset{|}{C}-F$ | 1 | Butyl | Ethyl | Propyl |
| 462 | $=\overset{|}{C}-F$ | 1 | Butyl | Ethyl | Butyl |
| 463 | $=\overset{|}{C}-F$ | 1 | Butyl | Propyl | Propyl |
| 464 | $=\overset{|}{C}-F$ | 1 | Butyl | Propyl | Butyl |
| 465 | $=\overset{|}{C}-F$ | 1 | Butyl | Butyl | Butyl |
| 466 | $=\overset{|}{C}-H$ | 2 | Methyl | H | H |
| 467 | $=\overset{|}{C}-H$ | 2 | Methyl | H | Methyl |
| 468 | $=\overset{|}{C}-H$ | 2 | Methyl | H | Ethyl |
| 469 | $=\overset{|}{C}-H$ | 2 | Methyl | H | Propyl |
| 470 | $=\overset{|}{C}-H$ | 2 | Methyl | H | Butyl |
| 471 | $=\overset{|}{C}-H$ | 2 | Methyl | Methyl | Methyl |
| 472 | $=\overset{|}{C}-H$ | 2 | Methyl | Methyl | Ethyl |
| 473 | $=\overset{|}{C}-H$ | 2 | Methyl | Methyl | Propyl |
| 474 | $=\overset{|}{C}-H$ | 2 | Methyl | Methyl | Butyl |
| 475 | $=\overset{|}{C}-H$ | 2 | Methyl | Ethyl | Ethyl |
| 476 | $=\overset{|}{C}-H$ | 2 | Methyl | Ethyl | Propyl |
| 477 | $=\overset{|}{C}-H$ | 2 | Methyl | Ethyl | Butyl |
| 478 | $=\overset{|}{C}-H$ | 2 | Methyl | Propyl | Propyl |
| 479 | $=\overset{|}{C}-H$ | 2 | Methyl | Propyl | Butyl |
| 480 | $=\overset{|}{C}-H$ | 2 | Methyl | Butyl | Butyl |
| 481 | $=\overset{|}{C}-F$ | 2 | Methyl | H | H |

-continued

| Example | X | n | $R_1$ | $R_2$ | $R_3$ |
|---|---|---|---|---|---|
| 482 | $=\overset{|}{C}-F$ | 2 | Methyl | H | Methyl |
| 483 | $=\overset{|}{C}-F$ | 2 | Methyl | H | Ethyl |
| 484 | $=\overset{|}{C}-F$ | 2 | Methyl | H | Propyl |
| 485 | $=\overset{|}{C}-F$ | 2 | Methyl | H | Butyl |
| 486 | $=\overset{|}{C}-F$ | 2 | Methyl | Methyl | Methyl |
| 487 | $=\overset{|}{C}-F$ | 2 | Methyl | Methyl | Ethyl |
| 488 | $=\overset{|}{C}-F$ | 2 | Methyl | Methyl | Propyl |
| 489 | $=\overset{|}{C}-F$ | 2 | Methyl | Methyl | Butyl |
| 490 | $=\overset{|}{C}-F$ | 2 | Methyl | Ethyl | Ethyl |
| 491 | $=\overset{|}{C}-F$ | 2 | Methyl | Ethyl | Propyl |
| 492 | $=\overset{|}{C}-F$ | 2 | Methyl | Ethyl | Butyl |
| 493 | $=\overset{|}{C}-F$ | 2 | Methyl | Propyl | Propyl |
| 494 | $=\overset{|}{C}-F$ | 2 | Methyl | Propyl | Butyl |
| 495 | $=\overset{|}{C}-F$ | 2 | Methyl | Butyl | Butyl |
| 496 | =C—H | 2 | Ethyl | H | H |
| 497 | =C—H | 2 | Ethyl | H | Methyl |
| 498 | =C—H | 2 | Ethyl | H | Ethyl |
| 499 | $=\overset{|}{C}-H$ | 2 | Ethyl | H | Propyl |
| 500 | $=\overset{|}{C}-H$ | 2 | Ethyl | H | Butyl |
| 501 | $=\overset{|}{C}-H$ | 2 | Ethyl | Methyl | Methyl |
| 502 | $=\overset{|}{C}-H$ | 2 | Ethyl | Methyl | Ethyl |
| 503 | $=\overset{|}{C}-H$ | 2 | Ethyl | Methyl | Propyl |
| 504 | $=\overset{|}{C}-H$ | 2 | Ethyl | Methyl | Butyl |
| 505 | =C—H | 2 | Ethyl | Ethyl | Ethyl |

-continued

| Example | X | n | R₁ | R₂ | R₃ |
|---|---|---|---|---|---|
| 506 | =C-H | 2 | Ethyl | Ethyl | Propyl |
| 507 | =C-H | 2 | Ethyl | Ethyl | Butyl |
| 508 | =C-H | 2 | Ethyl | Propyl | Propyl |
| 509 | =C-H | 2 | Ethyl | Propyl | Butyl |
| 510 | =C-H | 2 | Ethyl | Butyl | Butyl |
| 511 | =C-F | 2 | Ethyl | H | H |
| 512 | =C-F | 2 | Ethyl | H | Methyl |
| 513 | =C-F | 2 | Ethyl | H | Ethyl |
| 514 | =C-F | 2 | Ethyl | H | Propyl |
| 515 | =C-F | 2 | Ethyl | H | Butyl |
| 516 | =C-F | 2 | Ethyl | Methyl | Methyl |
| 517 | =C-F | 2 | Ethyl | Methyl | Ethyl |
| 518 | =C-F | 2 | Ethyl | Methyl | Propyl |
| 519 | =C-H | 2 | Ethyl | Methyl | Butyl |
| 520 | =C-F | 2 | Ethyl | Ethyl | Ethyl |
| 521 | =C-F | 2 | Ethyl | Ethyl | Propyl |
| 522 | =C-F | 2 | Ethyl | Ethyl | Butyl |
| 523 | =C-F | 2 | Ethyl | Propyl | Propyl |
| 524 | =C-F | 2 | Ethyl | Propyl | Butyl |
| 525 | =C-F | 2 | Ethyl | Butyl | Butyl |
| 526 | =C-H | 2 | Propyl | H | H |
| 527 | =C-H | 2 | Propyl | H | Methyl |

5,260,286
-continued

| Example | X | n | R₁ | R₂ | R₃ |
|---|---|---|---|---|---|
| 528 | =C−H | 2 | Propyl | H | Ethyl |
| 529 | =C−H | 2 | Propyl | H | Propyl |
| 530 | =C−H | 2 | Propyl | H | Butyl |
| 531 | =C−H | 2 | Propyl | Methyl | Methyl |
| 532 | =C−H | 2 | Propyl | Methyl | Ethyl |
| 533 | =C−H | 2 | Propyl | Methyl | Propyl |
| 534 | =C−H | 2 | Propyl | Methyl | Butyl |
| 535 | =C−H | 2 | Propyl | Ethyl | Ethyl |
| 536 | =C−H | 2 | Propyl | Ethyl | Propyl |
| 537 | =C−H | 2 | Propyl | Ethyl | Butyl |
| 538 | =C−H | 2 | Propyl | Propyl | Propyl |
| 539 | =C−H | 2 | Propyl | Propyl | Butyl |
| 540 | =C−H | 2 | Propyl | Butyl | Butyl |
| 541 | =C−F | 2 | Propyl | H | H |
| 542 | =C−F | 2 | Propyl | H | Methyl |
| 543 | =C−F | 2 | Propyl | H | Ethyl |
| 544 | =C−F | 2 | Propyl | H | Propyl |
| 545 | =C−F | 2 | Propyl | H | Butyl |
| 546 | =C−F | 2 | Propyl | Methyl | Methyl |
| 547 | =C−F | 2 | Propyl | Methyl | Ethyl |
| 548 | =C−F | 2 | Propyl | Methyl | Propyl |
| 549 | =C−F | 2 | Propyl | Methyl | Butyl |
| 550 | =C−F | 2 | Propyl | Ethyl | Ethyl |
| 551 | =C−F | 2 | Propyl | Ethyl | Propyl |

-continued

| Example | X | n | R₁ | R₂ | R₃ |
|---|---|---|---|---|---|
| 552 | =C-F | 2 | Propyl | Ethyl | Butyl |
| 553 | =C-F | 2 | Propyl | Propyl | Propyl |
| 554 | =C-F | 2 | Propyl | Propyl | Butyl |
| 555 | =C-F | 2 | Propyl | Butyl | Butyl |
| 556 | =C-H | 2 | Butyl | H | H |
| 557 | =C-H | 2 | Butyl | H | Methyl |
| 558 | =C-H | 2 | Butyl | H | Ethyl |
| 559 | =C-H | 2 | Butyl | H | Propyl |
| 560 | =C-H | 2 | Butyl | H | Butyl |
| 561 | =C-H | 2 | Butyl | Methyl | Methyl |
| 562 | =C-H | 2 | Butyl | Methyl | Ethyl |
| 563 | =C-H | 2 | Butyl | Methyl | Propyl |
| 564 | =C-H | 2 | Butyl | Methyl | Butyl |
| 565 | =C-H | 2 | Butyl | Ethyl | Ethyl |
| 566 | =C-H | 2 | Butyl | Ethyl | Propyl |
| 567 | =C-H | 2 | Butyl | Ethyl | Butyl |
| 568 | =C-H | 2 | Butyl | Propyl | Propyl |
| 569 | =C-H | 2 | Butyl | Propyl | Butyl |
| 570 | =C-H | 2 | Butyl | Butyl | Butyl |
| 571 | =C-F | 2 | Butyl | H | H |
| 572 | =C-F | 2 | Butyl | H | Methyl |

-continued

| Example | X | n | R₁ | R₂ | R₃ |
|---|---|---|---|---|---|
| 573 | =C−F | 2 | Butyl | H | Ethyl |
| 574 | =C−F | 2 | Butyl | H | Propyl |
| 575 | =C−F | 2 | Butyl | H | Butyl |
| 576 | =C−F | 2 | Butyl | Methyl | Methyl |
| 577 | =C−F | 2 | Butyl | Methyl | Ethyl |
| 578 | =C−F | 2 | Butyl | Methyl | Propyl |
| 579 | =C−F | 2 | Butyl | Methyl | Butyl |
| 580 | =C−F | 2 | Butyl | Ethyl | Ethyl |
| 581 | =C−F | 2 | Butyl | Ethyl | Propyl |
| 582 | =C−F | 2 | Butyl | Ethyl | Butyl |
| 583 | =C−F | 2 | Butyl | Propyl | Propyl |
| 584 | =C−F | 2 | Butyl | Propyl | Butyl |
| 585 | =C−F | 2 | Butyl | Butyl | Butyl |
| 586 | =C−H | 3 | Methyl | H | H |
| 587 | =C−H | 3 | Methyl | H | Methyl |
| 588 | =C−H | 3 | Methyl | H | Ethyl |
| 589 | =C−H | 3 | Methyl | H | Propyl |
| 590 | =C−H | 3 | Methyl | H | Butyl |
| 591 | =C−H | 3 | Methyl | Methyl | Methyl |
| 592 | =C−H | 3 | Methyl | Methyl | Ethyl |
| 593 | =C−H | 3 | Methyl | Methyl | Propyl |
| 594 | =C−H | 3 | Methyl | Methyl | Butyl |
| 595 | =C−H | 3 | Methyl | Ethyl | Ethyl |

-continued

| Example | X | n | $R_1$ | $R_2$ | $R_3$ |
|---|---|---|---|---|---|
| 596 | =C-H | 3 | Methyl | Ethyl | Propyl |
| 597 | =C-H | 3 | Methyl | Ethyl | Butyl |
| 598 | =C-H | 3 | Methyl | Propyl | Propyl |
| 599 | =C-H | 3 | Methyl | Propyl | Butyl |
| 600 | =C-H | 3 | Methyl | Butyl | Butyl |
| 601 | =C-F | 3 | Methyl | H | H |
| 602 | =C-F | 3 | Methyl | H | Methyl |
| 603 | =C-F | 3 | Methyl | H | Ethyl |
| 604 | =C-F | 3 | Methyl | H | Propyl |
| 605 | =C-F | 3 | Methyl | H | Butyl |
| 606 | =C-F | 3 | Methyl | Methyl | Methyl |
| 607 | =C-F | 3 | Methyl | Methyl | Ethyl |
| 608 | =C-F | 3 | Methyl | Methyl | Propyl |
| 609 | =C-F | 3 | Methyl | Methyl | Butyl |
| 610 | =C-F | 3 | Methyl | Ethyl | Ethyl |
| 611 | =C-F | 3 | Methyl | Ethyl | Propyl |
| 612 | =C-F | 3 | Methyl | Ethyl | Butyl |
| 613 | =C-F | 3 | Methyl | Propyl | Propyl |
| 614 | =C-F | 3 | Methyl | Propyl | Butyl |
| 615 | =C-F | 3 | Methyl | Butyl | Butyl |
| 616 | =C-H | 3 | Ethyl | H | H |
| 617 | =C-H | 3 | Ethyl | H | Methyl |
| 618 | =C-H | 3 | Ethyl | H | Ethyl |
| 619 | =C-H | 3 | Ethyl | H | Propyl |

-continued

| Example | X | n | R₁ | R₂ | R₃ |
|---|---|---|---|---|---|
| 620 | =C—H | 3 | Ethyl | H | Butyl |
| 621 | =C—H | 3 | Ethyl | Methyl | Methyl |
| 622 | =C—H | 3 | Ethyl | Methyl | Ethyl |
| 623 | =C—H | 3 | Ethyl | Methyl | Propyl |
| 624 | =C—H | 3 | Ethyl | Methyl | Butyl |
| 625 | =C—H | 3 | Ethyl | Ethyl | Ethyl |
| 626 | =C—H | 3 | Ethyl | Ethyl | Propyl |
| 627 | =C—H | 3 | Ethyl | Ethyl | Butyl |
| 628 | =C—H | 3 | Ethyl | Propyl | Propyl |
| 629 | =C—H | 3 | Ethyl | Propyl | Butyl |
| 630 | =C—H | 3 | Ethyl | Butyl | Butyl |
| 631 | =C—F | 3 | Ethyl | H | H |
| 632 | =C—F | 3 | Ethyl | H | Methyl |
| 633 | =C—F | 3 | Ethyl | H | Ethyl |
| 634 | =C—F | 3 | Ethyl | H | Propyl |
| 635 | =C—F | 3 | Ethyl | H | Butyl |
| 636 | =C—F | 3 | Ethyl | Methyl | Methyl |
| 637 | =C—F | 3 | Ethyl | Methyl | Ethyl |
| 638 | =C—F | 3 | Ethyl | Methyl | Propyl |
| 639 | =C—F | 3 | Ethyl | Methyl | Butyl |
| 640 | =C—F | 3 | Ethyl | Ethyl | Ethyl |
| 641 | =C—F | 3 | Ethyl | Ethyl | Propyl |
| 642 | =C—F | 3 | Ethyl | Ethyl | Butyl |

-continued

| Example | X | n | R₁ | R₂ | R₃ |
|---|---|---|---|---|---|
| 643 | =C−F | 3 | Ethyl | Propyl | Propyl |
| 644 | =C−F | 3 | Ethyl | Propyl | Butyl |
| 645 | =C−F | 3 | Ethyl | Butyl | Butyl |
| 646 | =C−H | 3 | Propyl | H | H |
| 647 | =C−H | 3 | Propyl | H | Methyl |
| 648 | =C−H | 3 | Propyl | H | Ethyl |
| 649 | =C−H | 3 | Propyl | H | Propyl |
| 650 | =C−H | 3 | Propyl | H | Butyl |
| 651 | =C−H | 3 | Propyl | Methyl | Methyl |
| 652 | =C−H | 3 | Propyl | Methyl | Ethyl |
| 653 | =C−H | 3 | Propyl | Methyl | Propyl |
| 654 | =C−H | 3 | Propyl | Methyl | Butyl |
| 655 | =C−H | 3 | Propyl | Ethyl | Ethyl |
| 656 | =C−H | 3 | Propyl | Ethyl | Propyl |
| 657 | =C−H | 3 | Propyl | Ethyl | Butyl |
| 658 | =C−H | 3 | Propyl | Propyl | Propyl |
| 659 | =C−H | 3 | Propyl | Propyl | Butyl |
| 660 | =C−H | 3 | Propyl | Butyl | Butyl |
| 661 | =C−F | 3 | Propyl | H | H |
| 662 | =C−F | 3 | Propyl | H | Methyl |
| 663 | =C−F | 3 | Propyl | H | Ethyl |

-continued

| Example | X | n | $R_1$ | $R_2$ | $R_3$ |
|---|---|---|---|---|---|
| 664 | $=\overset{|}{C}-F$ | 3 | Propyl | H | Propyl |
| 665 | $=\overset{|}{C}-F$ | 3 | Propyl | H | Butyl |
| 666 | $=\overset{|}{C}-F$ | 3 | Propyl | Methyl | Methyl |
| 667 | $=\overset{|}{C}-F$ | 3 | Propyl | Methyl | Ethyl |
| 668 | $=\overset{|}{C}-F$ | 3 | Propyl | Methyl | Propyl |
| 669 | $=\overset{|}{C}-F$ | 3 | Propyl | Methyl | Butyl |
| 670 | $=\overset{|}{C}-F$ | 3 | Propyl | Ethyl | Ethyl |
| 671 | $=\overset{|}{C}-F$ | 3 | Propyl | Ethyl | Propyl |
| 672 | $=\overset{|}{C}-F$ | 3 | Propyl | Ethyl | Butyl |
| 673 | $=\overset{|}{C}-F$ | 3 | Propyl | Propyl | Propyl |
| 674 | $=\overset{|}{C}-F$ | 3 | Propyl | Propyl | Butyl |
| 675 | $=\overset{|}{C}-F$ | 3 | Propyl | Butyl | Butyl |
| 676 | $=C-H$ | 3 | Butyl | H | H |
| 677 | $=C-H$ | 3 | Butyl | H | Methyl |
| 678 | $=C-H$ | 3 | Butyl | H | Ethyl |
| 679 | $=\overset{|}{C}-H$ | 3 | Butyl | H | Propyl |
| 680 | $=\overset{|}{C}-H$ | 3 | Butyl | H | Butyl |
| 681 | $=\overset{|}{C}-H$ | 3 | Butyl | Methyl | Methyl |
| 682 | $=\overset{|}{C}-H$ | 3 | Butyl | Methyl | Ethyl |
| 683 | $=\overset{|}{C}-H$ | 3 | Butyl | Methyl | Propyl |
| 684 | $=\overset{|}{C}-H$ | 3 | Butyl | Methyl | Butyl |
| 685 | $=C-H$ | 3 | Butyl | Ethyl | Ethyl |
| 686 | $=\overset{|}{C}-H$ | 3 | Butyl | Ethyl | Propyl |
| 687 | $=\overset{|}{C}-H$ | 3 | Butyl | Ethyl | Butyl |

-continued

| Example | X | n | $R_1$ | $R_2$ | $R_3$ |
|---|---|---|---|---|---|
| 688 | =C-H | 3 | Butyl | Propyl | Propyl |
| 689 | =C-H | 3 | Butyl | Propyl | Butyl |
| 690 | =C-H | 3 | Butyl | Butyl | Butyl |
| 691 | =C-F | 3 | Propyl | H | H |
| 692 | =C-F | 3 | Butyl | H | Methyl |
| 693 | =C-F | 3 | Butyl | H | Ethyl |
| 694 | =C-F | 3 | Butyl | H | Propyl |
| 695 | =C-F | 3 | Butyl | H | Butyl |
| 696 | =C-F | 3 | Butyl | Methyl | Methyl |
| 697 | =C-F | 3 | Butyl | Methyl | Ethyl |
| 698 | =C-F | 3 | Butyl | Methyl | Propyl |
| 699 | =C-F | 3 | Butyl | Methyl | Butyl |
| 700 | =C-F | 3 | Butyl | Ethyl | Ethyl |
| 701 | =C-F | 3 | Butyl | Ethyl | Propyl |
| 702 | =C-F | 3 | Butyl | Ethyl | Butyl |
| 703 | =C-F | 3 | Butyl | Propyl | Propyl |
| 704 | =C-F | 3 | Butyl | Propyl | Butyl |
| 705 | =C-F | 3 | Butyl | Butyl | Butyl |
| 706 | =C-H | 4 | Methyl | H | H |
| 707 | =C-H | 4 | Methyl | H | Methyl |
| 708 | =C-H | 4 | Methyl | H | Ethyl |
| 709 | =C-H | 4 | Methyl | H | Propyl |
| 710 | =C-H | 4 | Methyl | H | Butyl |

-continued

| Example | X | n | R₁ | R₂ | R₃ |
|---|---|---|---|---|---|
| 711 | =C-H | 4 | Methyl | Methyl | Methyl |
| 712 | =C-H | 4 | Methyl | Methyl | Ethyl |
| 713 | =C-H | 4 | Methyl | Methyl | Propyl |
| 714 | =C-H | 4 | Methyl | Methyl | Butyl |
| 715 | =C-H | 4 | Methyl | Ethyl | Ethyl |
| 716 | =C-H | 4 | Methyl | Ethyl | Propyl |
| 717 | =C-H | 4 | Methyl | Ethyl | Butyl |
| 718 | =C-H | 4 | Methyl | Propyl | Propyl |
| 719 | =C-H | 4 | Methyl | Propyl | Butyl |
| 720 | =C-H | 4 | Methyl | Butyl | Butyl |
| 721 | =C-F | 4 | Methyl | H | H |
| 722 | =C-F | 4 | Methyl | H | Methyl |
| 723 | =C-F | 4 | Methyl | H | Ethyl |
| 724 | =C-F | 4 | Methyl | H | Propyl |
| 725 | =C-F | 4 | Methyl | H | Butyl |
| 726 | =C-F | 4 | Methyl | Methyl | Methyl |
| 727 | =C-F | 4 | Methyl | Methyl | Ethyl |
| 728 | =C-F | 4 | Methyl | Methyl | Propyl |
| 729 | =C-F | 4 | Methyl | Methyl | Butyl |
| 730 | =C-F | 4 | Methyl | Ethyl | Ethyl |
| 731 | =C-F | 4 | Methyl | Ethyl | Propyl |
| 732 | =C-F | 4 | Methyl | Ethyl | Butyl |
| 733 | =C-F | 4 | Methyl | Propyl | Propyl |
| 734 | =C-F | 4 | Methyl | Propyl | Butyl |
| 735 | =C-F | 4 | Methyl | Butyl | Butyl |
| 736 | =C-H | 4 | Ethyl | H | H |
| 737 | =C-H | 4 | Ethyl | H | Methyl |

-continued

| Example | X | n | R₁ | R₂ | R₃ |
|---|---|---|---|---|---|
| 738 | =C−H | 4 | Ethyl | H | Ethyl |
| 739 | =C−H | 4 | Ethyl | H | Propyl |
| 740 | =C−H | 4 | Ethyl | H | Butyl |
| 741 | =C−H | 4 | Ethyl | Methyl | Methyl |
| 742 | =C−H | 4 | Ethyl | Methyl | Ethyl |
| 743 | =C−H | 4 | Ethyl | Methyl | Propyl |
| 744 | =C−H | 4 | Ethyl | Methyl | Butyl |
| 745 | =C−H | 4 | Ethyl | Ethyl | Ethyl |
| 746 | =C−H | 4 | Ethyl | Ethyl | Propyl |
| 747 | =C−H | 4 | Ethyl | Ethyl | Butyl |
| 748 | =C−H | 4 | Ethyl | Propyl | Propyl |
| 749 | =C−H | 4 | Ethyl | Propyl | Butyl |
| 750 | =C−H | 4 | Ethyl | Butyl | Butyl |
| 751 | =C−F | 4 | Ethyl | H | H |
| 752 | =C−F | 4 | Ethyl | H | Methyl |
| 753 | =C−F | 4 | Ethyl | H | Ethyl |
| 754 | =C−F | 4 | Ethyl | H | Propyl |
| 755 | =C−F | 4 | Ethyl | H | Butyl |
| 756 | =C−F | 4 | Ethyl | Methyl | Methyl |
| 757 | =C−F | 4 | Ethyl | Methyl | Ethyl |
| 758 | =C−F | 4 | Ethyl | Methyl | Propyl |
| 759 | =C−F | 4 | Ethyl | Methyl | Butyl |
| 760 | =C−F | 4 | Ethyl | Ethyl | Ethyl |
| 761 | =C−F | 4 | Ethyl | Ethyl | Propyl |
| 762 | =C−F | 4 | Ethyl | Ethyl | Butyl |

-continued

| Example | X | n | R₁ | R₂ | R₃ |
|---|---|---|---|---|---|
| 763 | =C—F | 4 | Ethyl | Propyl | Propyl |
| 764 | =C—F | 4 | Ethyl | Propyl | Butyl |
| 765 | =C—F | 4 | Ethyl | Butyl | Butyl |
| 766 | =C—H | 4 | Propyl | H | H |
| 767 | =C—H | 4 | Propyl | H | Methyl |
| 768 | =C—H | 4 | Propyl | H | Ethyl |
| 769 | =C—H | 4 | Propyl | H | Propyl |
| 770 | =C—H | 4 | Propyl | H | Butyl |
| 771 | =C—H | 4 | Propyl | Methyl | Methyl |
| 772 | =C—H | 4 | Propyl | Methyl | Ethyl |
| 773 | =C—H | 4 | Propyl | Methyl | Propyl |
| 774 | =C—H | 4 | Propyl | Methyl | Butyl |
| 775 | =C—H | 4 | Propyl | Ethyl | Ethyl |
| 776 | =C—H | 4 | Propyl | Ethyl | Propyl |
| 777 | =C—H | 4 | Propyl | Ethyl | Butyl |
| 778 | =C—H | 4 | Propyl | Propyl | Propyl |
| 779 | =C—H | 4 | Propyl | Propyl | Butyl |
| 780 | =C—H | 4 | Propyl | Butyl | Butyl |
| 781 | =C—F | 4 | Propyl | H | H |
| 782 | =C—F | 4 | Propyl | H | Methyl |
| 783 | =C—F | 4 | Propyl | H | Ethyl |
| 784 | =C—F | 4 | Propyl | H | Propyl |

-continued

| Example | X | n | $R_1$ | $R_2$ | $R_3$ |
|---|---|---|---|---|---|
| 785 | $=\overset{\mid}{C}-F$ | 4 | Propyl | H | Butyl |
| 786 | $=\overset{\mid}{C}-F$ | 4 | Propyl | Methyl | Methyl |
| 787 | $=\overset{\mid}{C}-F$ | 4 | Propyl | Methyl | Ethyl |
| 788 | $=\overset{\mid}{C}-F$ | 4 | Propyl | Methyl | Propyl |
| 789 | $=\overset{\mid}{C}-F$ | 4 | Propyl | Methyl | Butyl |
| 790 | $=\overset{\mid}{C}-F$ | 4 | Propyl | Ethyl | Ethyl |
| 791 | $=\overset{\mid}{C}-F$ | 4 | Propyl | Ethyl | Propyl |
| 792 | $=\overset{\mid}{C}-F$ | 4 | Propyl | Ethyl | Butyl |
| 793 | $=\overset{\mid}{C}-F$ | 4 | Propyl | Propyl | Propyl |
| 794 | $=\overset{\mid}{C}-F$ | 4 | Propyl | Propyl | Butyl |
| 795 | $=\overset{\mid}{C}-F$ | 4 | Propyl | Butyl | Butyl |
| 796 | $=\overset{\mid}{C}-H$ | 4 | Butyl | H | H |
| 797 | $=C-H$ | 4 | Butyl | H | Methyl |
| 798 | $=\overset{\mid}{C}-H$ | 4 | Butyl | H | Ethyl |
| 799 | $=\overset{\mid}{C}-H$ | 4 | Butyl | H | Propyl |
| 800 | $=\overset{\mid}{C}-H$ | 4 | Butyl | H | Butyl |
| 801 | $=\overset{\mid}{C}-H$ | 4 | Butyl | Methyl | Methyl |
| 802 | $=\overset{\mid}{C}-H$ | 4 | Butyl | Methyl | Ethyl |
| 803 | $=\overset{\mid}{C}-H$ | 4 | Butyl | Methyl | Propyl |
| 804 | $=\overset{\mid}{C}-H$ | 4 | Butyl | Methyl | Butyl |
| 805 | $=\overset{\mid}{C}-H$ | 4 | Butyl | Ethyl | Ethyl |
| 806 | $=\overset{\mid}{C}-H$ | 4 | Butyl | Ethyl | Propyl |

-continued

| Example | X | n | R₁ | R₂ | R₃ |
|---------|---|---|-----|-----|-----|
| 807 | =C—H | 4 | Butyl | Ethyl | Butyl |
| 808 | =C—H | 4 | Butyl | Propyl | Propyl |
| 809 | =C—H | 4 | Butyl | Propyl | Butyl |
| 810 | =C—H | 4 | Butyl | Butyl | Butyl |
| 811 | =C—F | 4 | Butyl | H | H |
| 812 | =C—F | 4 | Butyl | H | Methyl |
| 813 | =C—F | 4 | Butyl | H | Ethyl |
| 814 | =C—F | 4 | Butyl | H | Propyl |
| 815 | =C—F | 4 | Butyl | H | Butyl |
| 816 | =C—F | 4 | Butyl | Methyl | Methyl |
| 817 | =C—F | 4 | Butyl | Methyl | Ethyl |
| 818 | =C—F | 4 | Butyl | Methyl | Propyl |
| 819 | =C—F | 4 | Butyl | Methyl | Butyl |
| 820 | =C—F | 4 | Butyl | Ethyl | Ethyl |
| 821 | =C—F | 4 | Butyl | Ethyl | Propyl |
| 822 | =C—F | 4 | Butyl | Ethyl | Butyl |
| 823 | =C—F | 4 | Butyl | Propyl | Propyl |
| 824 | =C—F | 4 | Butyl | Propyl | Butyl |
| 825 | =C—F | 4 | Butyl | Butyl | Butyl |
| 826 | =N—O— | 0 | Methyl | H | H |
| 827 | =N—O— | 0 | Methyl | H | Methyl |
| 828 | =N—O— | 0 | Methyl | H | Ethyl |
| 829 | =N—O— | 0 | Methyl | H | Propyl |
| 830 | =N—O— | 0 | Methyl | H | Butyl |
| 831 | =N—O— | 0 | Methyl | Methyl | Methyl |
| 832 | =N—O— | 0 | Methyl | Methyl | Ethyl |
| 833 | =N—O— | 0 | Methyl | Methyl | Propyl |
| 834 | =N—O— | 0 | Methyl | Methyl | Butyl |
| 835 | =N—O— | 0 | Methyl | Ethyl | Ethyl |

-continued

| Example | X | n | R$_1$ | R$_2$ | R$_3$ |
|---|---|---|---|---|---|
| 836 | =N—O— | 0 | Methyl | Ethyl | Propyl |
| 837 | =N—O— | 0 | Methyl | Ethyl | Butyl |
| 838 | =N—O— | 0 | Methyl | Propyl | Propyl |
| 839 | =N—O— | 0 | Methyl | Propyl | Butyl |
| 840 | =N—O— | 0 | Methyl | Butyl | Butyl |
| 841 | =N—O— | 1 | Methyl | H | H |
| 842 | =N—O— | 1 | Methyl | H | Methyl |
| 843 | =N—O— | 1 | Methyl | H | Ethyl |
| 844 | =N—O— | 1 | Methyl | H | Propyl |
| 845 | =N—O— | 1 | Methyl | H | Butyl |
| 846 | =N—O— | 1 | Methyl | Methyl | Methyl |
| 847 | =N—O— | 1 | Methyl | Methyl | Ethyl |
| 848 | =N—O— | 1 | Methyl | Methyl | Propyl |
| 849 | =N—O— | 1 | Methyl | Methyl | Butyl |
| 850 | =N—O— | 1 | Methyl | Ethyl | Ethyl |
| 851 | =N—O— | 1 | Methyl | Ethyl | Propyl |
| 852 | =N—O— | 1 | Methyl | Ethyl | Butyl |
| 853 | =N—O— | 1 | Methyl | Propyl | Propyl |
| 854 | =N—O— | 1 | Methyl | Propyl | Butyl |
| 855 | =N—O— | 1 | Methyl | Butyl | Butyl |
| 856 | =N—O— | 2 | Ethyl | H | H |
| 857 | =N—O— | 2 | Ethyl | H | Methyl |
| 858 | =N—O— | 2 | Ethyl | H | Ethyl |
| 859 | =N—O— | 2 | Ethyl | H | Propyl |
| 860 | =N—O— | 2 | Ethyl | H | Butyl |
| 861 | =N—O— | 2 | Ethyl | Methyl | Methyl |
| 862 | =N—O— | 2 | Ethyl | Methyl | Ethyl |
| 863 | =N—O— | 2 | Ethyl | Methyl | Propyl |
| 864 | =N—O— | 2 | Ethyl | Methyl | Butyl |
| 865 | =N—O— | 2 | Ethyl | Ethyl | Ethyl |
| 866 | =N—O— | 2 | Ethyl | Ethyl | Propyl |
| 867 | =N—O— | 2 | Ethyl | Ethyl | Butyl |
| 868 | =N—O— | 2 | Ethyl | Propyl | Propyl |
| 869 | =N—O— | 2 | Ethyl | Propyl | Butyl |
| 870 | =N—O— | 2 | Ethyl | Butyl | Butyl |
| 871 | =N—O— | 3 | Ethyl | H | H |
| 872 | =N—O— | 3 | Ethyl | H | Methyl |
| 873 | =N—O— | 3 | Ethyl | H | Ethyl |
| 874 | =N—O— | 3 | Ethyl | H | Propyl |
| 875 | =N—O— | 3 | Ethyl | H | Butyl |
| 876 | =N—O— | 3 | Ethyl | Methyl | Methyl |
| 877 | =N—O— | 3 | Ethyl | Methyl | Ethyl |
| 878 | =N—O— | 3 | Ethyl | Methyl | Propyl |
| 879 | =N—O— | 3 | Ethyl | Methyl | Butyl |
| 880 | =N—O— | 3 | Ethyl | Ethyl | Ethyl |
| 881 | =N—O— | 3 | Ethyl | Ethyl | Propyl |
| 882 | =N—O— | 3 | Ethyl | Ethyl | Butyl |
| 883 | =N—O— | 3 | Ethyl | Propyl | Propyl |
| 884 | =N—O— | 3 | Ethyl | Propyl | Butyl |
| 885 | =N—O— | 3 | Ethyl | Butyl | Butyl |
| 886 | =N—O— | 4 | Propyl | H | H |
| 887 | =N—O— | 4 | Propyl | H | Methyl |
| 888 | =N—O— | 4 | Propyl | H | Ethyl |
| 889 | =N—O— | 4 | Propyl | H | Propyl |
| 890 | =N—O— | 4 | Propyl | H | Butyl |
| 891 | =N—O— | 4 | Propyl | Methyl | Methyl |
| 892 | =N—O— | 4 | Propyl | Methyl | Ethyl |
| 893 | =N—O— | 4 | Propyl | Methyl | Propyl |
| 894 | =N—O— | 4 | Propyl | Methyl | Butyl |
| 895 | =N—O— | 4 | Propyl | Ethyl | Ethyl |
| 896 | =N—O— | 4 | Propyl | Ethyl | Propyl |
| 897 | =N—O— | 4 | Propyl | Ethyl | Butyl |
| 898 | =N—O— | 4 | Propyl | Propyl | Propyl |
| 899 | =N—O— | 4 | Propyl | Propyl | Butyl |
| 900 | =N—O— | 4 | Propyl | Butyl | Butyl |
| 901 | =N—O— | 0 | Propyl | H | H |
| 902 | =N—O— | 0 | Propyl | H | Methyl |
| 903 | =N—O— | 0 | Propyl | H | Ethyl |
| 904 | =N—O— | 0 | Propyl | H | Propyl |
| 905 | =N—O— | 0 | Propyl | H | Butyl |
| 906 | =N—O— | 0 | Propyl | Methyl | Methyl |
| 907 | =N—O— | 0 | Propyl | Methyl | Ethyl |
| 908 | =N—O— | 0 | Propyl | Methyl | Propyl |
| 909 | =N—O— | 0 | Propyl | Methyl | Butyl |
| 910 | =N—O— | 0 | Propyl | Ethyl | Ethyl |
| 911 | =N—O— | 0 | Propyl | Ethyl | Propyl |
| 912 | =N—O— | 0 | Propyl | Ethyl | Butyl |
| 913 | =N—O— | 0 | Propyl | Propyl | Propyl |
| 914 | =N—O— | 0 | Propyl | Propyl | Butyl |
| 915 | =N—O— | 0 | Propyl | Butyl | Butyl |
| 916 | =N—O— | 0 | Butyl | H | H |

-continued

| Example | X | n | R₁ | R₂ | R₃ |
|---------|-----|---|--------|--------|--------|
| 917 | =N—O— | 0 | Butyl | H | Methyl |
| 918 | =N—O— | 0 | Butyl | H | Ethyl |
| 919 | =N—O— | 0 | Butyl | H | Propyl |
| 920 | =N—O— | 0 | Butyl | H | Butyl |
| 921 | =N—O— | 0 | Butyl | Methyl | Methyl |
| 922 | =N—O— | 0 | Butyl | Methyl | Ethyl |
| 923 | =N—O— | 0 | Butyl | Methyl | Propyl |
| 924 | =N—O— | 0 | Butyl | Methyl | Butyl |
| 925 | =N—O— | 0 | Butyl | Ethyl | Ethyl |
| 926 | =N—O— | 0 | Butyl | Ethyl | Propyl |
| 927 | =N—O— | 0 | Butyl | Ethyl | Butyl |
| 928 | =N—O— | 0 | Butyl | Propyl | Propyl |
| 929 | =N—O— | 0 | Butyl | Propyl | Butyl |
| 930 | =N—O— | 0 | Butyl | Butyl | Butyl |
| 931 | =N—O— | 0 | Butyl | H | H |
| 932 | =N—O— | 1 | Butyl | H | Methyl |
| 933 | =N—O— | 1 | Butyl | H | Ethyl |
| 934 | =N—O— | 1 | Butyl | H | Propyl |
| 935 | =N—O— | 1 | Butyl | H | Butyl |
| 936 | =N—O— | 1 | Butyl | Methyl | Methyl |
| 937 | =N—O— | 1 | Butyl | Methyl | Ethyl |
| 938 | =N—O— | 1 | Butyl | Methyl | Propyl |
| 939 | =N—O— | 1 | Butyl | Methyl | Butyl |
| 940 | =N—O— | 1 | Butyl | Ethyl | Ethyl |
| 941 | =N—O— | 1 | Butyl | Ethyl | Propyl |
| 942 | =N—O— | 1 | Butyl | Ethyl | Butyl |
| 943 | =N—O— | 1 | Butyl | Propyl | Propyl |
| 944 | =N—O— | 1 | Butyl | Propyl | Butyl |
| 945 | =N—O— | 1 | Butyl | Butyl | Butyl |
| 946 | =N—O— | 2 | Methyl | H | H |
| 947 | =N—O— | 2 | Methyl | H | Methyl |
| 948 | =N—O— | 2 | Methyl | H | Ethyl |
| 949 | =N—O— | 2 | Methyl | H | Propyl |
| 950 | =N—O— | 2 | Methyl | H | Butyl |
| 951 | =N—O— | 2 | Methyl | Methyl | Methyl |
| 952 | =N—O— | 2 | Methyl | Methyl | Ethyl |
| 953 | =N—O— | 2 | Methyl | Methyl | Propyl |
| 954 | =N—O— | 2 | Methyl | Methyl | Butyl |
| 955 | =N—O— | 2 | Methyl | Ethyl | Ethyl |
| 956 | =N—O— | 2 | Methyl | Ethyl | Propyl |
| 957 | =N—O— | 2 | Methyl | Ethyl | Butyl |
| 958 | =N—O— | 2 | Methyl | Propyl | Propyl |
| 959 | =N—O— | 2 | Methyl | Propyl | Butyl |
| 960 | =N—O— | 2 | Methyl | Butyl | Butyl |
| 961 | =N—O— | 3 | Methyl | H | H |
| 962 | =N—O— | 3 | Methyl | H | Methyl |
| 963 | =N—O— | 3 | Methyl | H | Ethyl |
| 964 | =N—O— | 3 | Methyl | H | Propyl |
| 965 | =N—O— | 3 | Methyl | H | Butyl |
| 966 | =N—O— | 3 | Methyl | Methyl | Methyl |
| 967 | =N—O— | 3 | Methyl | Methyl | Ethyl |
| 968 | =N—O— | 3 | Methyl | Methyl | Propyl |
| 969 | =N—O— | 3 | Methyl | Methyl | Butyl |
| 970 | =N—O— | 3 | Methyl | Ethyl | Ethyl |
| 971 | =N—O— | 3 | Methyl | Ethyl | Propyl |
| 972 | =N—O— | 3 | Methyl | Ethyl | Butyl |
| 973 | =N—O— | 3 | Methyl | Propyl | Propyl |
| 974 | =N—O— | 3 | Methyl | Propyl | Butyl |
| 975 | =N—O— | 3 | Methyl | Butyl | Butyl |
| 976 | =N—O— | 4 | Ethyl | H | H |
| 977 | =N—O— | 4 | Ethyl | H | Methyl |
| 978 | =N—O— | 4 | Ethyl | H | Ethyl |
| 979 | =N—O— | 4 | Ethyl | H | Propyl |
| 980 | =N—O— | 4 | Ethyl | H | Butyl |
| 981 | =N—O— | 4 | Ethyl | Methyl | Methyl |
| 982 | =N—O— | 4 | Ethyl | Methyl | Ethyl |
| 983 | =N—O— | 4 | Ethyl | Methyl | Propyl |
| 984 | =N—O— | 4 | Ethyl | Methyl | Butyl |
| 985 | =N—O— | 4 | Ethyl | Ethyl | Ethyl |
| 986 | =N—O— | 4 | Ethyl | Ethyl | Propyl |
| 987 | =N—O— | 4 | Ethyl | Ethyl | Butyl |
| 988 | =N—O— | 4 | Ethyl | Propyl | Propyl |
| 989 | =N—O— | 4 | Ethyl | Propyl | Butyl |
| 990 | =N—O— | 4 | Ethyl | Butyl | Butyl |
| 991 | =N—O— | 0 | Ethyl | H | H |
| 992 | =N—O— | 0 | Ethyl | H | Methyl |
| 993 | =N—O— | 0 | Ethyl | H | Ethyl |
| 994 | =N—O— | 0 | Ethyl | H | Propyl |
| 995 | =N—O— | 0 | Ethyl | H | Butyl |
| 996 | =N—O— | 0 | Ethyl | Methyl | Methyl |
| 997 | =N—O— | 0 | Ethyl | Methyl | Ethyl |

-continued

| Example | X | n | R₁ | R₂ | R₃ |
|---|---|---|---|---|---|
| 998 | =N—O— | 0 | Ethyl | Methyl | Propyl |
| 999 | =N—O— | 0 | Ethyl | Methyl | Butyl |
| 1000 | =N—O— | 0 | Ethyl | Ethyl | Ethyl |
| 1001 | =N—O— | 0 | Ethyl | Ethyl | Propyl |
| 1002 | =N—O— | 0 | Ethyl | Ethyl | Butyl |
| 1003 | =N—O— | 0 | Ethyl | Propyl | Propyl |
| 1004 | =N—O— | 0 | Ethyl | Propyl | Butyl |
| 1005 | =N—O— | 0 | Ethyl | Butyl | Butyl |
| 1006 | =N—O— | 1 | Propyl | H | H |
| 1007 | =N—O— | 1 | Propyl | H | Methyl |
| 1008 | =N—O— | 1 | Propyl | H | Ethyl |
| 1009 | =N—O— | 1 | Propyl | H | Propyl |
| 1010 | =N—O— | 1 | Propyl | H | Butyl |
| 1011 | =N—O— | 1 | Propyl | Methyl | Methyl |
| 1012 | =N—O— | 1 | Propyl | Methyl | Ethyl |
| 1013 | =N—O— | 1 | Propyl | Methyl | Propyl |
| 1014 | =N—O— | 1 | Propyl | Methyl | Butyl |
| 1015 | =N—O— | 1 | Propyl | Ethyl | Ethyl |
| 1016 | =N—O— | 1 | Propyl | Ethyl | Propyl |
| 1017 | =N—O— | 1 | Propyl | Ethyl | Butyl |
| 1018 | =N—O— | 1 | Propyl | Propyl | Propyl |
| 1019 | =N—O— | 1 | Propyl | Propyl | Butyl |
| 1020 | =N—O— | 1 | Propyl | Butyl | Butyl |
| 1021 | =N—O— | 2 | Propyl | H | H |
| 1022 | =N—O— | 2 | Propyl | H | Methyl |
| 1023 | =N—O— | 2 | Propyl | H | Ethyl |
| 1024 | =N—O— | 2 | Propyl | H | Propyl |
| 1025 | =N—O— | 2 | Propyl | H | Butyl |
| 1026 | =N—O— | 2 | Propyl | Methyl | Methyl |
| 1027 | =N—O— | 2 | Propyl | Methyl | Ethyl |
| 1028 | =N—O— | 2 | Propyl | Methyl | Propyl |
| 1029 | =N—O— | 2 | Propyl | Methyl | Butyl |
| 1030 | =N—O— | 2 | Propyl | Ethyl | Ethyl |
| 1031 | =N—O— | 2 | Propyl | Ethyl | Propyl |
| 1032 | =N—O— | 2 | Propyl | Ethyl | Butyl |
| 1033 | =N—O— | 2 | Propyl | Propyl | Propyl |
| 1034 | =N—O— | 2 | Propyl | Propyl | Butyl |
| 1035 | =N—O— | 2 | Propyl | Butyl | Butyl |
| 1036 | =N—O— | 3 | Butyl | H | H |
| 1037 | =N—O— | 3 | Butyl | H | Methyl |
| 1038 | =N—O— | 3 | Butyl | H | Ethyl |
| 1039 | =N—O— | 3 | Butyl | H | Propyl |
| 1040 | =N—O— | 3 | Butyl | H | Butyl |
| 1041 | =N—O— | 3 | Butyl | Methyl | Methyl |
| 1042 | =N—O— | 3 | Butyl | Methyl | Ethyl |
| 1043 | =N—O— | 3 | Butyl | Methyl | Propyl |
| 1044 | =N—O— | 3 | Butyl | Methyl | Butyl |
| 1045 | =N—O— | 3 | Butyl | Ethyl | Ethyl |
| 1046 | =N—O— | 3 | Butyl | Ethyl | Propyl |
| 1047 | =N—O— | 3 | Butyl | Ethyl | Butyl |
| 1048 | =N—O— | 3 | Butyl | Propyl | Propyl |
| 1049 | =N—O— | 3 | Butyl | Propyl | Butyl |
| 1050 | =N—O— | 3 | Butyl | Butyl | Butyl |
| 1051 | =N—O— | 4 | Butyl | H | H |
| 1052 | =N—O— | 4 | Butyl | H | Methyl |
| 1053 | =N—O— | 4 | Butyl | H | Ethyl |
| 1054 | =N—O— | 4 | Butyl | H | Propyl |
| 1055 | =N—O— | 4 | Butyl | H | Butyl |
| 1056 | =N—O— | 4 | Butyl | Methyl | Methyl |
| 1057 | =N—O— | 4 | Butyl | Methyl | Ethyl |
| 1058 | =N—O— | 4 | Butyl | Methyl | Propyl |
| 1059 | =N—O— | 4 | Butyl | Methyl | Butyl |
| 1060 | =N—O— | 4 | Butyl | Ethyl | Ethyl |
| 1061 | =N—O— | 4 | Butyl | Ethyl | Propyl |
| 1062 | =N—O— | 4 | Butyl | Ethyl | Butyl |
| 1063 | =N—O— | 4 | Butyl | Propyl | Propyl |
| 1064 | =N—O— | 4 | Butyl | Propyl | Butyl |
| 1065 | =N—O— | 4 | Butyl | Butyl | Butyl |
| 1066 | =N—O— | 4 | Methyl | H | H |
| 1067 | =N—O— | 4 | Methyl | H | Methyl |
| 1068 | =N—O— | 4 | Methyl | H | Ethyl |
| 1069 | =N—O— | 4 | Methyl | H | Propyl |
| 1070 | =N—O— | 4 | Methyl | H | Butyl |
| 1071 | =N—O— | 4 | Methyl | Methyl | Methyl |
| 1072 | =N—O— | 4 | Methyl | Methyl | Ethyl |
| 1073 | =N—O— | 4 | Methyl | Methyl | Propyl |
| 1074 | =N—O— | 4 | Methyl | Methyl | Butyl |
| 1075 | =N—O— | 4 | Methyl | Ethyl | Ethyl |
| 1076 | =N—O— | 4 | Methyl | Ethyl | Propyl |
| 1077 | =N—O— | 4 | Methyl | Ethyl | Butyl |
| 1078 | =N—O— | 4 | Methyl | Propyl | Propyl |

-continued

| Example | X | n | R₁ | R₂ | R₃ |
|---|---|---|---|---|---|
| 1079 | =N—O— | 4 | Methyl | Propyl | Butyl |
| 1080 | =N—O— | 4 | Methyl | Butyl | Butyl |
| 1081 | =N—O— | 2 | Butyl | H | H |
| 1082 | =N—O— | 2 | Butyl | H | Methyl |
| 1083 | =N—O— | 2 | Butyl | H | Ethyl |
| 1084 | =N—O— | 2 | Butyl | H | Propyl |
| 1085 | =N—O— | 2 | Butyl | H | Butyl |
| 1086 | =N—O— | 2 | Butyl | Methyl | Methyl |
| 1087 | =N—O— | 2 | Butyl | Methyl | Ethyl |
| 1088 | =N—O— | 2 | Butyl | Methyl | Propyl |
| 1089 | =N—O— | 2 | Butyl | Methyl | Butyl |
| 1090 | =N—O— | 2 | Butyl | Ethyl | Ethyl |
| 1091 | =N—O— | 2 | Butyl | Ethyl | Propyl |
| 1092 | =N—O— | 2 | Butyl | Ethyl | Butyl |
| 1093 | =N—O— | 2 | Butyl | Propyl | Propyl |
| 1094 | =N—O— | 2 | Butyl | Propyl | Butyl |
| 1095 | =N—O— | 2 | Butyl | Butyl | Butyl |
| 1096 | =N—O— | 1 | Ethyl | H | H |
| 1097 | =N—O— | 1 | Ethyl | H | Methyl |
| 1098 | =N—O— | 1 | Ethyl | H | Ethyl |
| 1099 | =N—O— | 1 | Ethyl | H | Propyl |
| 1100 | =N—O— | 1 | Ethyl | H | Butyl |
| 1101 | =N—O— | 1 | Ethyl | Methyl | Methyl |
| 1102 | =N—O— | 1 | Ethyl | Methyl | Ethyl |
| 1103 | =N—O— | 1 | Ethyl | Methyl | Propyl |
| 1104 | =N—O— | 1 | Ethyl | Methyl | Butyl |
| 1105 | =N—O— | 1 | Ethyl | Ethyl | Ethyl |
| 1106 | =N—O— | 1 | Ethyl | Ethyl | Propyl |
| 1107 | =N—O— | 1 | Ethyl | Ethyl | Butyl |
| 1108 | =N—O— | 1 | Ethyl | Propyl | Propyl |
| 1109 | =N—O— | 1 | Ethyl | Propyl | Butyl |
| 1110 | =N—O— | 1 | Ethyl | Butyl | Butyl |
| 1111 | =N—O— | 3 | Ethyl | H | H |
| 1112 | =N—O— | 3 | Propyl | H | Methyl |
| 1113 | =N—O— | 3 | Propyl | H | Ethyl |
| 1114 | =N—O— | 3 | Propyl | H | Propyl |
| 1115 | =N—O— | 3 | Propyl | H | Butyl |
| 1116 | =N—O— | 3 | Propyl | Methyl | Methyl |
| 1117 | =N—O— | 3 | Propyl | Methyl | Ethyl |
| 1118 | =N—O— | 3 | Propyl | Methyl | Propyl |
| 1119 | =N—O— | 3 | Propyl | Methyl | Butyl |
| 1120 | =N—O— | 3 | Propyl | Ethyl | Ethyl |
| 1121 | =N—O— | 3 | Propyl | Ethyl | Propyl |
| 1122 | =N—O— | 3 | Propyl | Ethyl | Butyl |
| 1123 | =N—O— | 3 | Propyl | Propyl | Propyl |
| 1124 | =N—O— | 3 | Propyl | Propyl | Butyl |
| 1125 | =N—O— | 3 | Propyl | Butyl | Butyl |

We claim:

1. A compound of the formula

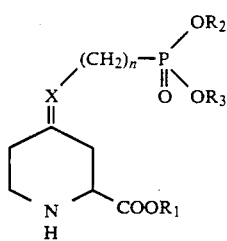

wherein X is

or =N—O—, in which R₄ is hydrogen or halogen, R₁, R₂, and R₃ independently represent hydrogen or a C$_{1-4}$ alkyl group, and n is an integer having a value of zero to four inclusive and pharmaceutically acceptable salts thereof.

2. The compound of claim 1 wherein R₁, R₂ and R₃ independently represent hydrogen or a methyl group and pharmaceutically acceptable salts thereof.

3. The compound of claim 1 wherein n has a value of zero to two and pharmaceutically acceptable salts thereof.

4. The compound of claim 1 wherein X is

in which R₄ is hydrogen or halogen and pharmaceutically acceptable salts thereof.

5. The compound of claim 1 wherein X is =H—O— and pharmaceutically acceptable salts thereof.

6. A pharmaceutical composition comprising an effective amount of the compound or salt of claim 1 admixed with a pharmaceutically acceptable carrier.

7. A method to block N-methyl-D-aspartate receptors comprising administering to a subject in need thereof an effective amount of the pharmaceutical composition of claim 6.

8. A method to treat pathosis or diseases having a relation with N-methyl-D-aspartate receptors comprising administering to a subject in need thereof an effective amount of the pharmaceutical composition of claim 6.

9. A method to treat cerebral ischemia, cerebral hypoglycemia, epilepsy, anxiety or convulsion comprising administering to a subject in need thereof an effective amount of the pharmaceutical composition of claim 6.

* * * * *